(12) United States Patent
Toth et al.

(10) Patent No.: US 12,310,760 B2
(45) Date of Patent: May 27, 2025

(54) MONITORING AND PROCESSING PHYSIOLOGICAL SIGNALS TO DETECT AND PREDICT DYSFUNCTION OF AN ANATOMICAL FEATURE OF AN INDIVIDUAL

(71) Applicant: LifeLens Technologies, Inc., Ivyland, PA (US)

(72) Inventors: Landy Toth, Doylestown, PA (US); Robert S. Schwartz, Inver Grove Heights, MN (US); Jonathan G. Schwartz, Charlotte, NC (US)

(73) Assignee: LifeLens Technologies, LLC, Ivyland, PA (US)

( * ) Notice: Subject to any disclaimer, the term of this patent is extended or adjusted under 35 U.S.C. 154(b) by 589 days.

(21) Appl. No.: 17/609,220

(22) PCT Filed: May 7, 2020

(86) PCT No.: PCT/US2020/031851
§ 371 (c)(1),
(2) Date: Nov. 5, 2021

(87) PCT Pub. No.: WO2020/227514
PCT Pub. Date: Nov. 12, 2020

(65) Prior Publication Data
US 2022/0211328 A1   Jul. 7, 2022

Related U.S. Application Data

(60) Provisional application No. 62/844,851, filed on May 8, 2019.

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0205* (2013.01); *G06N 3/02* (2013.01);
(Continued)

(58) Field of Classification Search
CPC ... A61B 5/7275; A61B 5/0205; A61B 5/7267; G16H 50/20; G16H 50/70; G16H 50/30
See application file for complete search history.

(56) References Cited

U.S. PATENT DOCUMENTS 11,331,508 B1 * 5/2022 Cowan .................... A61B 5/01
2002/0062139 A1   5/2002 Ding
(Continued)

FOREIGN PATENT DOCUMENTS

EP    20802525.4    12/2022
WO  PCT/US2020/031851    9/2020

OTHER PUBLICATIONS

Kimura-Medorima et al., P-wave duration is a predictor for long-term mortality in post-CABG, Plos One, https://doi.org/10.137/journal.pone.0199718, pp. 1-10 (Year: 2018).*

(Continued)

*Primary Examiner* — Catherine M Voorhees
(74) *Attorney, Agent, or Firm* — Ryan, Mason & Lewis, LLP

(57) ABSTRACT

Systems and methods are provided for monitoring and processing physiological signals (e.g., electrocardiogram signals) to detect and predict for possible dysfunction of an anatomical feature (e.g., cardiac dysfunction) or otherwise predict a likelihood of future cardiac dysfunction of the individual. For example, a system comprises a plurality of sensors, a physiological signal processing system, and a feature analysis system. The sensors are configured to monitor physiological signals from an individual that has undergone a medical procedure on an anatomical feature. The (Continued)

physiological signal processing system is configured to analyze the physiological signals and extract features from the physiological signals which are indicative of a function of the anatomical feature. The feature analysis system is configured to analyze the extracted features and predict a risk of the individual developing a post-procedural dysfunction of the anatomical feature as a result of the medical procedure on the anatomical feature.

20 Claims, 12 Drawing Sheets

(51) Int. Cl.
    G06N 3/02    (2006.01)
    G16H 50/20    (2018.01)
    G16H 50/70    (2018.01)
    A61B 5/361    (2021.01)
    A61B 5/363    (2021.01)
    G06N 3/08    (2023.01)
    G16H 50/30    (2018.01)

(52) U.S. Cl.
    CPC ............. *G16H 50/20* (2018.01); *G16H 50/70* (2018.01); *A61B 5/361* (2021.01); *A61B 5/363* (2021.01); *A61B 5/7267* (2013.01); *G06N 3/08* (2013.01); *G16H 50/30* (2018.01)

(56) References Cited

U.S. PATENT DOCUMENTS

| | | | |
|---|---|---|---|
| 2008/0167567 A1* | 7/2008 | Bashour | A61B 5/352 600/521 |
| 2010/0234716 A1* | 9/2010 | Engel | A61B 5/6833 600/459 |
| 2011/0130670 A1 | 6/2011 | Macquarrie et al. | |
| 2011/0224565 A1* | 9/2011 | Ong | A61B 5/4824 600/509 |
| 2013/0204149 A1 | 8/2013 | Hwang et al. | |
| 2016/0038093 A1* | 2/2016 | Sharma | G16H 20/00 600/481 |
| 2016/0135706 A1 | 5/2016 | Sullivan et al. | |
| 2017/0143268 A1* | 5/2017 | Kovacs | A61B 5/6887 |
| 2018/0199884 A1* | 7/2018 | Huppert | A61M 37/00 |
| 2020/0345273 A1* | 11/2020 | Daskivich | A61B 5/681 |

OTHER PUBLICATIONS

S.T. Kimura-Medorima et al., "P-Wave Duration is a Predictor for Long-Term Mortality in Post-CABG Patients," https://journals.plos.org/plosone/article/file?, Jul. 11, 2018, 13 pages.

M.J. Dayer et al., "Incidence of Infective Endocarditis in England, 2000-13: A Secular Trend, Interrupted Time-Series Analysis," https://thevalveclub.com.br/wp-content/uploads/2019/06/Post15_dayer2015.pdf, Nov. 18, 2014, 10 pages.

D. Li et al., "Electrocardiomatrix: A New Method for Beat-by-Beat Visualization and Inspection of Cardiac Signals," https://www.oatext.com/pdf/JIC-1-133.pdf, Sep. 24, 2015, pp. 124-128, vol. 1, No. 5.

M.M. Gallagher et al., "Electrocardiogramarkers of Structural Heart Disease and Predictors of Death in 2332 Unselected Patients Undergoing Outpatient Holter Recording," https://academic.oup.com/europace/article/9/12/1203/585625, Oct. 25, 2017, pp. 1203-1208, vol. 9.

M.G. Whitebeck et al., "QRS Duration Predicts Death and Hospitalization Among Patients with Atrial Fibrillation Irrespective of Heart Failure: Evidence from the AFFIRM Study," https://www.ncbi.nim.nih.gov/pmc/articles/PMC4305520/, Dec. 23, 2013, pp. 803-811, vol. 16.

S.K. Yadav et al., "Electrocardiogram Signal Denoising Using Nonlocal Wavelet Transform Domain Filtering," https://arxiv.org/pdf/1611.03320.pdf, Oct. 20, 2016, 9 pages.

Phidias, "Report on Feasibility of Analog Compressive Sampling Platform Implementation for Consortium Use," https://cordis.europa.eu/docs/project/cnect/3/318013/080/deliverables/001-D21reviewv13.pdf, Aug. 9, 2011, 19 pages.

Farah Shamout, Machine Learning for the Deterioration of Patients on Hospital Wards, http://www.robots.ox.ac.uk/-davidc/pubs/transfer_fs.pdf, Aug. 24, 2017, 45 pages.

Examination Report, dated Jan. 9, 2024, for counterpart India Application No. 202147056689.

* cited by examiner

200

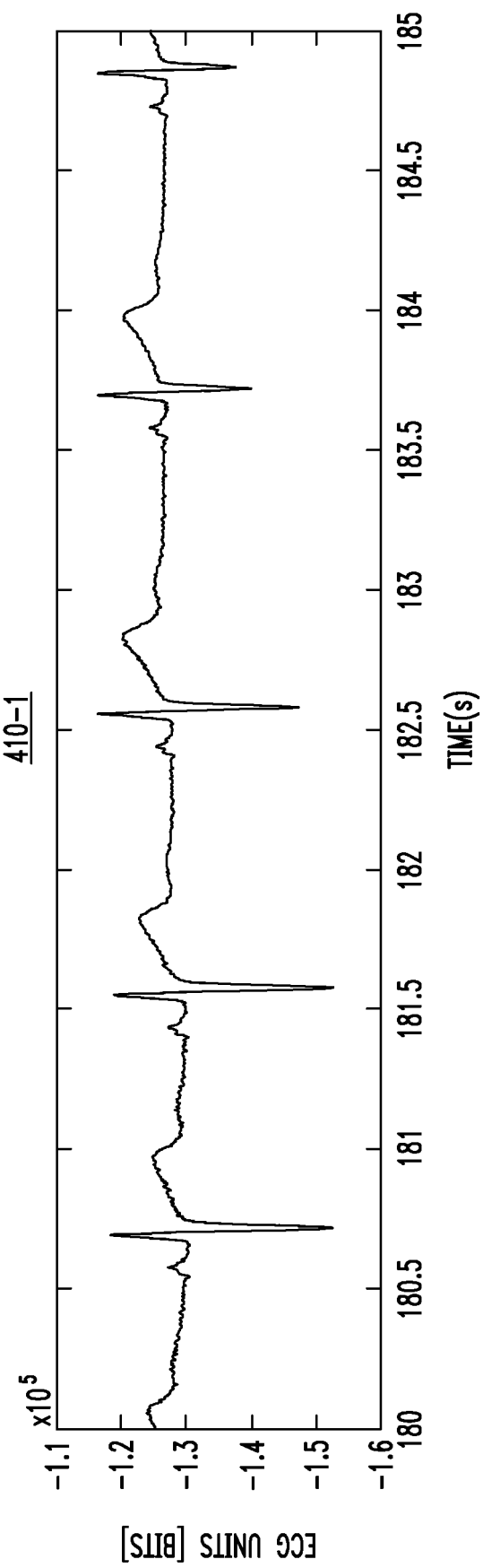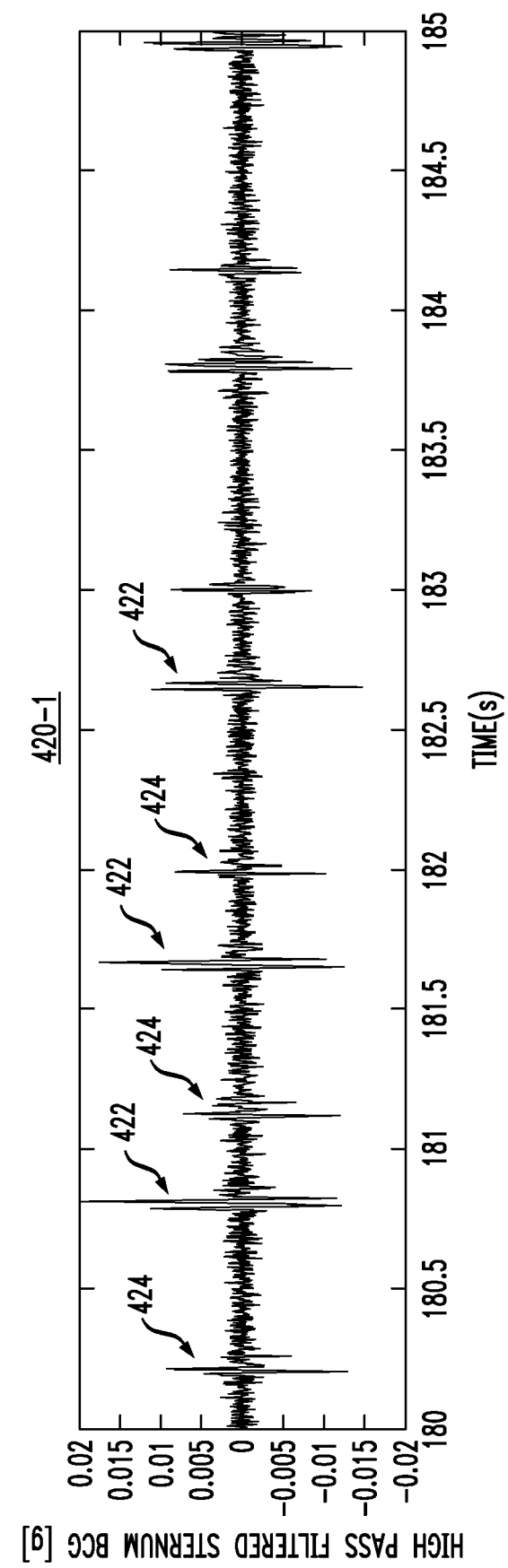
FIG. 4A

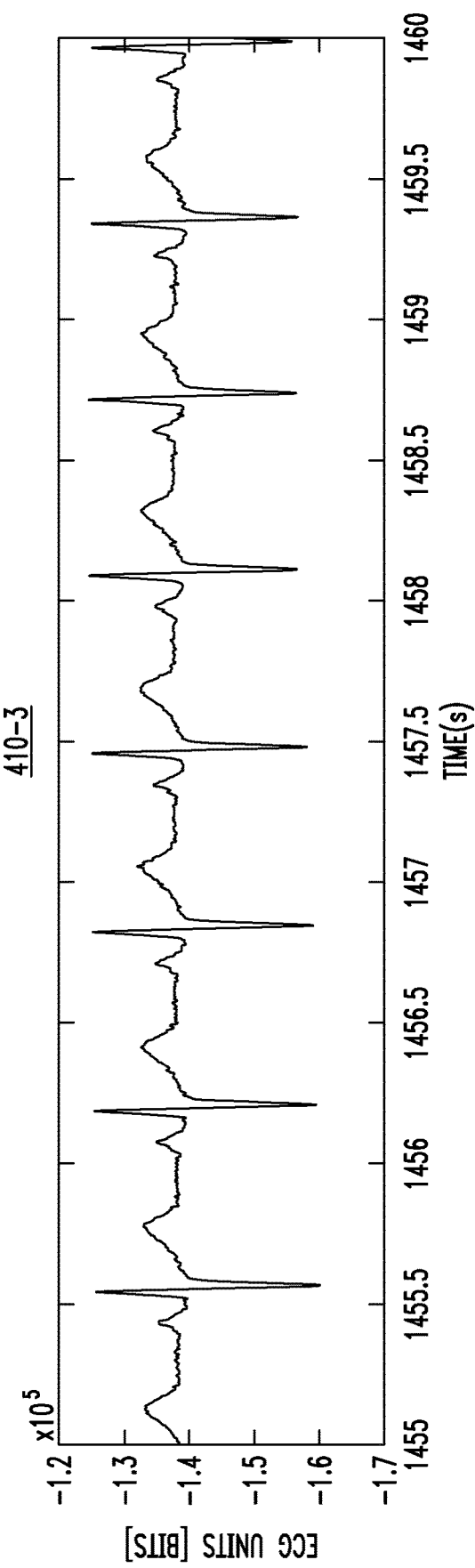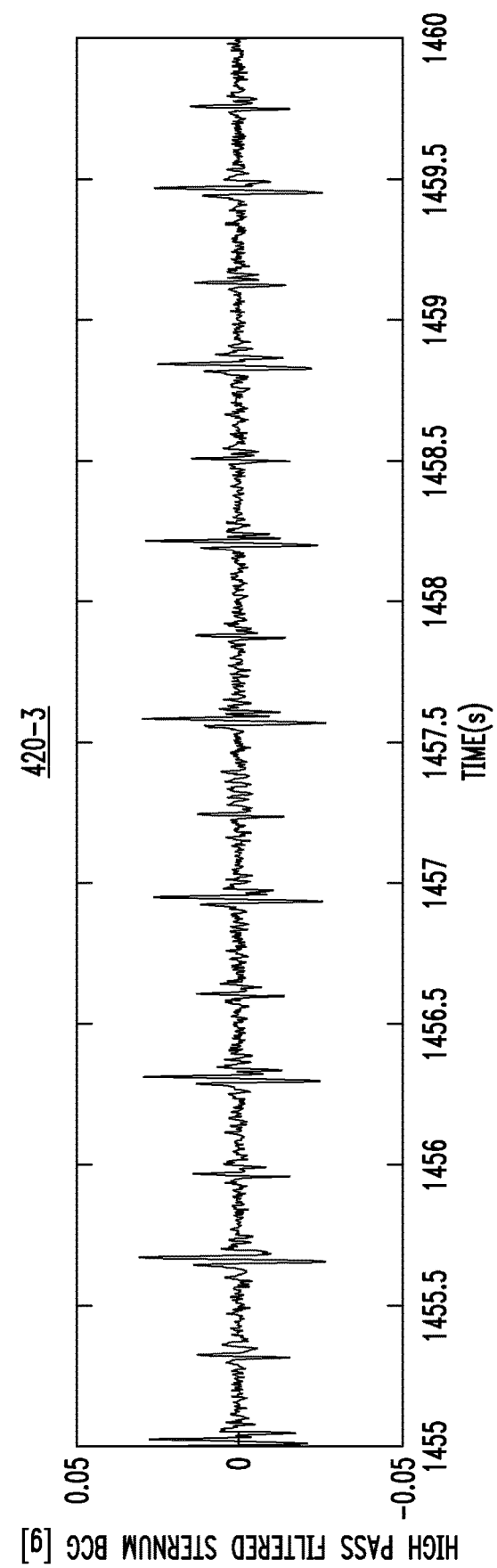
FIG. 4C

MONITORING AND PROCESSING PHYSIOLOGICAL SIGNALS TO DETECT AND PREDICT DYSFUNCTION OF AN ANATOMICAL FEATURE OF AN INDIVIDUAL

CROSS-REFERENCE TO RELATED APPLICATIONS

This application is a U.S. National Stage Application of International Application No. PCT/US2020/031851, filed on May 7, 2020, which claims the benefit of and priority to U.S. Provisional Application Ser. No. 62/844,851, filed on May 8, 2019, the disclosures of which are fully incorporated by reference herein for all purposes.

TECHNICAL FIELD

This disclosure relates generally to systems and methods for monitoring and processing physiological signals (e.g., electrocardiogram signals) to detect and predict possible dysfunction of an anatomical feature (e.g., cardiac dysfunction) following a medical procedure on the anatomical feature (e.g., structural heart intervention).

BACKGROUND

Electrophysiology is the study of the electrical properties of biological cells and tissue, and generally involves obtaining and processing measurements of changes in voltage or electrical current in biological tissue or in entire organs such as a heart. Electrophysiology techniques involve placing electrodes in contact with biological tissue at target regions within an organ using a medical device, such as a diagnostic catheter device, or using sensor electrodes that are attached to an individual's skin in target locations. Advances in medical technology and medical procedures have led to significant advances in the ability to treat valvular heart disease and anatomic cardiac defects utilizing catheter-based approaches. Such structural heart interventions include transcatheter aortic valve replacement, percutaneous mitral valve repair, septal defect closures, shunt interventions, paravalvular leak closures, balloon aortic valvuloplasty, and left atrial appendage closure. However, a structural heart intervention can lead to interruption or degradation of normal heart functionality (e.g., intracardiac conduction) due to electrical or mechanical pressures resulting from such structural heart intervention.

SUMMARY

Embodiments of the disclosure generally include systems and methods for monitoring and processing physiological signals (e.g., electrocardiogram signals) to detect and predict for possible dysfunction of an anatomical feature (e.g., cardiac dysfunction) or otherwise predict a likelihood of future cardiac dysfunction of the individual.

In one exemplary embodiment of the disclosure, a system comprises a plurality of sensors, a physiological signal processing system, and a feature analysis system. The sensors are configured to monitor physiological signals from an individual that has undergone a medical procedure on an anatomical feature. The physiological signal processing system is configured to analyze the physiological signals and extract features from the physiological signals which are indicative of a function of the anatomical feature following the medical procedure on the anatomical feature. The feature analysis system is configured to analyze the extracted features and predict a risk of the individual developing a post-procedural dysfunction of the anatomical feature as a result of the medical procedure on the anatomical feature.

In some embodiments, the sensors comprise sensor devices that are worn by the individual.

In some embodiments, the sensors comprise sensor patches that are coupled to the individual's skin.

In some embodiments, the physiological signal processing system is configured to extract features from the physiological signals that are obtained over a target monitoring period following the medical procedure, wherein the target monitoring period is one of: (i) less than an hour, (ii) about an hour, (iii) multiple hours, (iv) about a day, (v) multiple days, (vi) about a week, and (viii) multiple weeks, and wherein the physiological signals are obtained and analyzed one of continuously and intermittently during the target monitoring period.

In some embodiments, the medical procedure comprises a structural heart procedure and the physiological signals comprise an electrocardiogram signal.

In some embodiments, the physiological signal processing system is configured to analyze the electrocardiogram signal and extract a plurality of features indicative of intra-cardiac conduction over a plurality of cardiac cycles, wherein the plurality of extracted features comprise one or more of (i) waveform features comprising one or more of P-waves, T-waves, QRS-waves, U-waves, R-R intervals, PR timing intervals, QT timing intervals, QRS timing intervals, ST segments, and PR segments and (ii) morphological features of the waveform features.

In some embodiments, the morphological features of the waveform features comprise one or more of waveform shape, waveform contour, waveform amplitude, waveform width, waveform phase, waveform polarity, a notch, a local inversion, a ripple, an amplitude change, relative timing or polarity inversion thereof, a perturbation, a repetitive perturbation, a low amplitude, high frequency wavelet, a wavelet that repeats along with essentially a same period as a parent waveform.

In some embodiments, the feature analysis system is configured to (i) compute a trend line for at least one extracted feature of the plurality of extracted features based on time series data collected for the at least one extracted feature, (ii) compare the computed trend line with known trend lines for the at least one extracted feature as determined from a cohort patient population and (iii) risk stratify the computed trend line based on a result of comparing of the computed trend line with the known trend lines.

In some embodiments, the system further comprises a display system, wherein the feature analysis system is configured to render and display at least one of the time series data and the computed trend line for the at least one extracted feature on the display.

In some embodiments, the feature analysis system is configured to risk stratify the computed trend line into one of a plurality of zones comprising a low risk zone, an increasing risk zone, and a high-risk zone.

In some embodiments, the feature analysis system is configured to generate an alert notification when an extracted feature is determined to enter into a high-risk zone.

In some embodiments, the feature analysis system is configured to process time series data of at least one extracted feature of the plurality of extracted features using a neural network, and classify a risk profile of the at least one extracted feature based on processing results of the time series data applied to the neural network.

In some embodiments, the physiological signals further comprise one or more secondary physiological signals comprising an electromyogram signal, a respiratory rhythm signal, blood pressure signal, blood pressure surrogate waveform signal, a heart movement signal, a body movement signal, a phonogram, and a cardiac output signal, and the physiological signal processing system is configured to (i) time synchronize the electrocardiogram signal with the one or more secondary physiological signals and (ii) organize the cardiac cycles of the electrocardiogram signal into self-similar groups based on the time synchronized signals.

In some embodiments, the physiological signal processing system is configured to extract and compare the plurality of features of cardiac cycles within the same self-similar group.

In another exemplary embodiment, a system comprises a plurality of sensors, a signal processing system, and a feature analysis system. The sensors are configured to monitor electrocardiogram signals of an individual that has undergone a structural heart procedure. The signal processing system is configured to extract features from the electrocardiogram signals which are indicative of intracardiac conduction over a plurality of cardiac cycles, wherein the extracted features comprise waveform features comprising one or more of P-waves, T-waves, QRS-waves, and U-waves. The feature analysis system is configured to analyze the extracted features and predict a risk of the individual developing a heart dysfunction during a monitoring period subsequent to the structural heart procedure.

In some embodiments, the feature analysis system is configured to (i) compute a trend line for at least one extracted feature of the plurality of extracted features based on time series data collected for the at least one extracted feature, (ii) compare the computed trend line with known trend lines for the at least one extracted feature as determined from a cohort patient population, and (iii) risk stratify the computed trend line based on a result of comparing of the computed trend line with the known trend lines.

In some embodiments, the system further comprises a display system, wherein the feature analysis system is configured to render and display at least one of the time series data and the computed trend line for the at least one extracted feature on the display.

In some embodiments, the feature analysis system is configured to (i) risk stratify the computed trend line into one of a plurality of zones comprising a low risk zone, an increasing risk zone, and a high risk zone and (ii) generate an alert notification when an extracted feature is determined to enter into a high risk zone.

In some embodiments, the feature analysis system is configured to (i) utilize a neural network to process time series data of at least one extracted feature of the plurality of extracted features, which time series data are obtained over at least a portion of the monitoring period, and (ii) classify a risk profile of the at least one extracted feature based on processing results of the time series data applied to the neural network.

In some embodiments, the signal processing system is configured to determine a PR-timing interval between P and R waves over the plurality of cardiac cycles, and the feature analysis system is configured to determine a trend of the PR-timing intervals over at least a portion of the monitoring period subsequent to the structural heart procedure.

In some embodiments, the feature analysis system is configured to predict a risk of the individual developing a heart dysfunction during the monitoring period subsequent to the structural heart procedure in response to determining that the trend of the PR-timing interval indicates an increase in the PR-timing interval by more than a predetermined percentage subsequent to the structural heart procedure.

In some embodiments, the signal processing system is configured to (i) determine a PR-timing interval between P and R waves over the plurality of cardiac cycles, (ii) determine an R-R interval between successive cardiac cycles of the plurality of cardiac cycles, and (iii) normalize the PR-timing intervals between successive cardiac cycles based on the determined R-R intervals between successive heartbeats to thereby generate a time series of normalized PR-timing intervals. The feature analysis system is configured to determine a trend of the normalized PR-timing intervals over at least a portion of the monitoring period subsequent to the structural heart procedure.

In some embodiments, the feature analysis system is configured to predict a risk of the individual developing a heart dysfunction during the monitoring period subsequent to the structural heart procedure in response to determining that the trend of the normalized PR-timing intervals indicates an increase in the normalized PR-timing interval by more than a predetermined percentage subsequent to the structural heart procedure.

In some embodiments, the signal processing system is configured to determine one or more intracardiac conduction events from microfeatures associated with one or more of the P-waves and QRS-waves. The feature analysis system is configured to determine a trend of the determined intracardiac conduction events over at least a portion of the monitoring period subsequent to the structural heart procedure.

In some embodiments, the signal processing system is configured to determine a QS-timing interval over the plurality of cardiac cycles, and the feature analysis system is configured to determine a trend of the QS-timing intervals over at least a portion of the monitoring period subsequent to the structural heart procedure.

In some embodiments, the feature analysis system is configured to predict a risk of the individual developing a heart dysfunction during the monitoring period subsequent to the structural heart procedure in response to determining that the trend of the QS-timing intervals indicates an increase in the QS-timing interval by more than a predetermined percentage subsequent to the structural heart procedure.

In some embodiments, the signal processing system is configured to (i) determine a QS-timing interval between P and S waves over the plurality of cardiac cycles, (ii) determine an R-R interval between successive cardiac cycles of the plurality of cardiac cycles, and (iii) normalize the QS-timing intervals between successive cardiac cycles based on the determined R-R intervals between successive heartbeats to thereby generate a time series of normalized QS-timing intervals. The feature analysis system is configured to determine a trend of the normalized QS-timing intervals over at least a portion of the monitoring period subsequent to the structural heart procedure.

In some embodiments, the feature analysis system is configured to predict a risk of the individual developing a heart dysfunction during the monitoring period subsequent to the structural heart procedure in response to determining that the trend of the normalized QS-timing intervals indicates an increase in the normalized QS-timing interval by more than a predetermined percentage subsequent to the structural heart procedure.

In some embodiments, the signal processing system is configured to determine a QRS-waveform width over the plurality of cardiac cycles, and the feature analysis system is configured to determine a trend in changes of the QRS waveform width over at least a portion of the monitoring period subsequent to the structural heart procedure.

In some embodiments, the signal processing system is configured to determine a morphological feature of the QRS-waveforms over the plurality of cardiac cycles, and the feature analysis system is configured to determine a trend in changes of the morphological feature of the QRS waveforms over at least a portion of the monitoring period subsequent to the structural heart procedure.

In some embodiments, the sensors are configured to monitor one or more secondary physiological signals comprising an electromyogram signal, a respiratory rhythm signal, blood pressure signal, blood pressure surrogate waveform signal, a heart movement signal, a body movement signal, a phonogram, and a cardiac output signal. The physiological signal processing system is configured to (i) time synchronize the electrocardiogram signals with the one or more secondary physiological signals and (ii) organize the cardiac cycles of the electrocardiogram signals into self-similar groups based on the time synchronized signals.

In some embodiments, the physiological signal processing system is configured to compare the extracted features of cardiac cycles within the same self-similar group.

In some embodiments, (i) the electrocardiogram signals comprise a bandwidth in a range of about 0.01 Hz to about 1000 Hz, (ii) the waveform features in the electrocardiogram signals comprise P-waves and U-waves comprising a signal to noise ratio in a range of about 20 dB to about 40 dB, and (iii) the electrocardiogram signals comprise a noise floor of about 3 uV rms or less or about 1 uV rms or less.

In some embodiments, the sensors comprise sensor devices that are worn by the individual, and the physiological signal processing system and the feature analysis system are integrated within one or more of the sensor devices worn by the individual.

In some embodiments, the sensors comprise sensor patches that are coupled to the individual's skin, and the physiological signal processing system and the feature analysis system are integrated within one or more of the sensor patches.

In yet another exemplary embodiment of the disclosure, a system comprises a plurality of sensors, a signal processing system, and a feature analysis system. The sensors are configured to monitor electrocardiogram signals of an individual. The signal processing system is configured to extract a waveform feature from the electrocardiogram signals over a plurality of cardiac cycles. The feature analysis system is configured to analyze the extracted waveform feature over the plurality of cardiac cycles to: (i) determine a trend in changes of the extracted waveform feature over the plurality of cardiac cycles; (ii) compare the determined trend to known trends in changes of the extracted waveform feature for developing a heart dysfunction as determined from a cohort patient population; and (iii) predict a risk level of the individual developing the heart dysfunction based on a result of comparing the determined trend to the known trends.

In some embodiments, the extracted waveform feature comprises at least one of P-waves, T-waves, QRS-waves, U-waves, R-R intervals, PR-timing intervals, QT-timing intervals, QS-timing intervals, ST segments, and PR segments, and the changes of the extracted waveform feature comprise changes in morphological features of the extracted waveform feature.

In some embodiments, the morphological features of the extracted waveform features comprise one or more of waveform shape, waveform contour, waveform amplitude, waveform width, waveform phase, and waveform polarity.

In some embodiments, the sensors are configured to monitor one or more secondary physiological signals comprising an electromyogram signal, a respiratory rhythm signal, blood pressure signal, blood pressure surrogate waveform signal, a heart movement signal, a body movement signal, a phonogram, and a cardiac output signal; and the physiological signal processing system is configured to (i) time synchronize the electrocardiogram signals with the one or more secondary physiological signals and (ii) organize the cardiac cycles of the electrocardiogram signals into self-similar groups based on the time synchronized signals.

In some embodiments, the physiological signal processing system is configured to compare the extracted waveform features of cardiac cycles within the same self-similar group to determine a trend in changes of the extracted waveform feature in each of the self-similar groups over the plurality of cardiac cycles.

In some embodiments, (i) the electrocardiogram signals comprise a bandwidth in a range of about 0.01 Hz to about 500 Hz and (ii) the waveform features in the electrocardiogram signals comprise a signal to noise ratio in a range of about 10 dB to about 20 dB.

In some embodiments, the heart dysfunction comprises one or more of arrhythmia, atrial fibrillation, a heart block, an atrioventricular (AV) node block, a first degree AV block, a second-degree AV block, a type 2 second-degree AV block, a third degree AV block, a right bundle branch block, a left bundle branch block, angina, myocardial infarction, cardiogenic shock, cardiac arrest, and respiratory arrest.

In some embodiments, the feature analysis system is configured to (i) utilize a neural network to compare the determined trend to the known trends in changes of the extracted waveform feature, wherein the neural network is trained using a training dataset of the extracted waveform features obtained from the cohort patient population, and (ii) analyze processing results of the neural network to predict the risk level of the individual developing the heart dysfunction.

In another exemplary embodiment of the disclosure, a system comprises a plurality of sensors configured to monitor electrocardiogram signals, respiratory rhythm signals, torso posture, and an activity level of an individual over a plurality of respiratory cycles of the individual during a monitoring period, and a signal processing system configured to (i) parse the monitoring period into one or more regions wherein the monitored activity level is determined to be below a threshold level, (ii) determine groups of similarly classified cardiac cycles of the electrocardiogram signals which fall within the parsed regions based on a time synchronization of each cardiac cycle within the respiratory cycles and the torso posture of the individual, (iii) extract waveform features in each group of similarly classified cardiac cycles in each of the parsed regions, (iv) determine a trend in changes of the extracted waveform feature of each group of similarly classified cardiac cycles (v) compare the determined trends to known trends in changes of the extracted waveform feature for developing a heart dysfunction as determined from a cohort patient population, and (vi) predict a risk level of the individual developing the heart dysfunction based on a result of comparing the determined trends to the known trends.

In some embodiments, the signal processing system is further configured to (i) utilize a neural network to compare the determined trends to the known trends in changes of the extracted waveform features, wherein the neural network is trained using a training dataset of the extracted waveform features obtained from the cohort patient population, and (ii) analyze processing results of the neural network to predict the risk level of the individual developing the heart dysfunction.

In some embodiments, the sensors are configured to monitor cardiac movement of the individual, and the signal processing system is configured to extract one or more features associated with said cardiac movement.

In some embodiments, the cardiac movement comprises one or more of: a ventricular movement; an atrial movement; a left-heart contraction; a right-heart contraction; a left-heart expansion; a right-heart expansion; a valve closure; an aortic valve closure; a mitral valve closure; a tricuspid valve closure; and a pulmonic heart closure.

In some embodiments, the extracted waveform features comprise a P-wave, and the signal processing system is configured to (i) determine event features comprising a P-wave onset event and a valve closure event, (ii) combine the determined event features to generate time series event data for a P-wave to valve-closure delay, and (iii) determine a trend of the P-wave to valve-closure delay time series event data.

In another exemplary embodiment of the disclosure, a method comprises (i) monitoring physiological signals from an individual that has undergone a medical procedure on an anatomical feature, (ii) processing the physiological signals to extract features from the physiological signals which are indicative of a function of the anatomical feature following the medical procedure on the anatomical feature, and (iii) processing the extracted features to predict a risk of the individual developing a post-procedural dysfunction of the anatomical feature as a result of the medical procedure on the anatomical feature.

In another embodiment of the disclosure, a method comprises (i) monitoring electrocardiogram signals of an individual that has undergone a structural heart procedure, (ii) extracting features from the electrocardiogram signals which are indicative of intracardiac conduction over a plurality of cardiac cycles, wherein the plurality of extracted features comprise waveform features comprising one or more of P-waves, T-waves, QRS-waves, and U-waves, and (iii) processing the extracted features to predict a risk of the individual developing a heart dysfunction during a monitoring period subsequent to the structural heart procedure.

In another exemplary embodiment of the disclosure, a method comprises (i) monitoring electrocardiogram signals of an individual, (ii) extracting a waveform feature from the electrocardiogram signals over a plurality of cardiac cycles, (iii) analyzing the extracted waveform feature over the plurality of cardiac cycles to determine a trend in changes of the extracted waveform feature over the plurality of cardiac cycles, (iv) comparing the determined trend to known trends in changes of the extracted waveform feature for developing a heart dysfunction as determined from a cohort patient population, and (v) predicting a risk level of the individual developing the heart dysfunction based on a result of comparing the determined trend to the known trends.

In another exemplary embodiment of the disclosure, a method comprises (i) monitoring electrocardiogram signals, respiratory rhythm signals, torso posture, and an activity level of an individual over a plurality of respiratory cycles of the individual during a monitoring period, (ii) parsing the monitoring period into one or more regions wherein the monitored activity level is determined to be below a threshold level, (iii) determining groups of similarly classified cardiac cycles of the electrocardiogram signals which fall within the parsed regions, based on a time synchronization of each cardiac cycle within the respiratory cycles and the torso posture of the individual, (iv) extracting waveform features in each group of similarly classified cardiac cycles in each of the parsed regions, (v) determining a trend in changes of the extracted waveform feature of each group of similarly classified cardiac cycles, (vi) comparing the determined trends to known trends in changes of the extracted waveform feature for developing a heart dysfunction as determined from a cohort patient population, and (vii) predicting a risk level of the individual developing the heart dysfunction based on a result of comparing the determined trends to the known trends.

Other embodiments of the disclosure will be described in the following detailed description of embodiments, which is to be read in conjunction with the accompanying figures.

BRIEF DESCRIPTION OF THE DRAWINGS

FIGS. 4A, 4B and 4C schematically illustrate a method for time-synchronizing a primary physiological signal waveform and a secondary physiological signal waveform, according to an exemplary embodiment of the disclosure.

DETAILED DESCRIPTION

Embodiments of the disclosure will now be described in further detail with regard to systems and methods for monitoring and processing physiological signals to detect and predict for possible dysfunction of an anatomical feature following a medical procedure on the anatomical feature. While the exemplary system and methods described herein can be implemented for various types of anatomical features of an individual, for illustrative purposes, exemplary embodiments of the disclosure will be discussed in the context of processing physiological signals to detect and predict for possible cardiac dysfunction of an individual, or otherwise predict a likelihood of a future onset of cardiac dysfunction of the individual.

Figure 1:
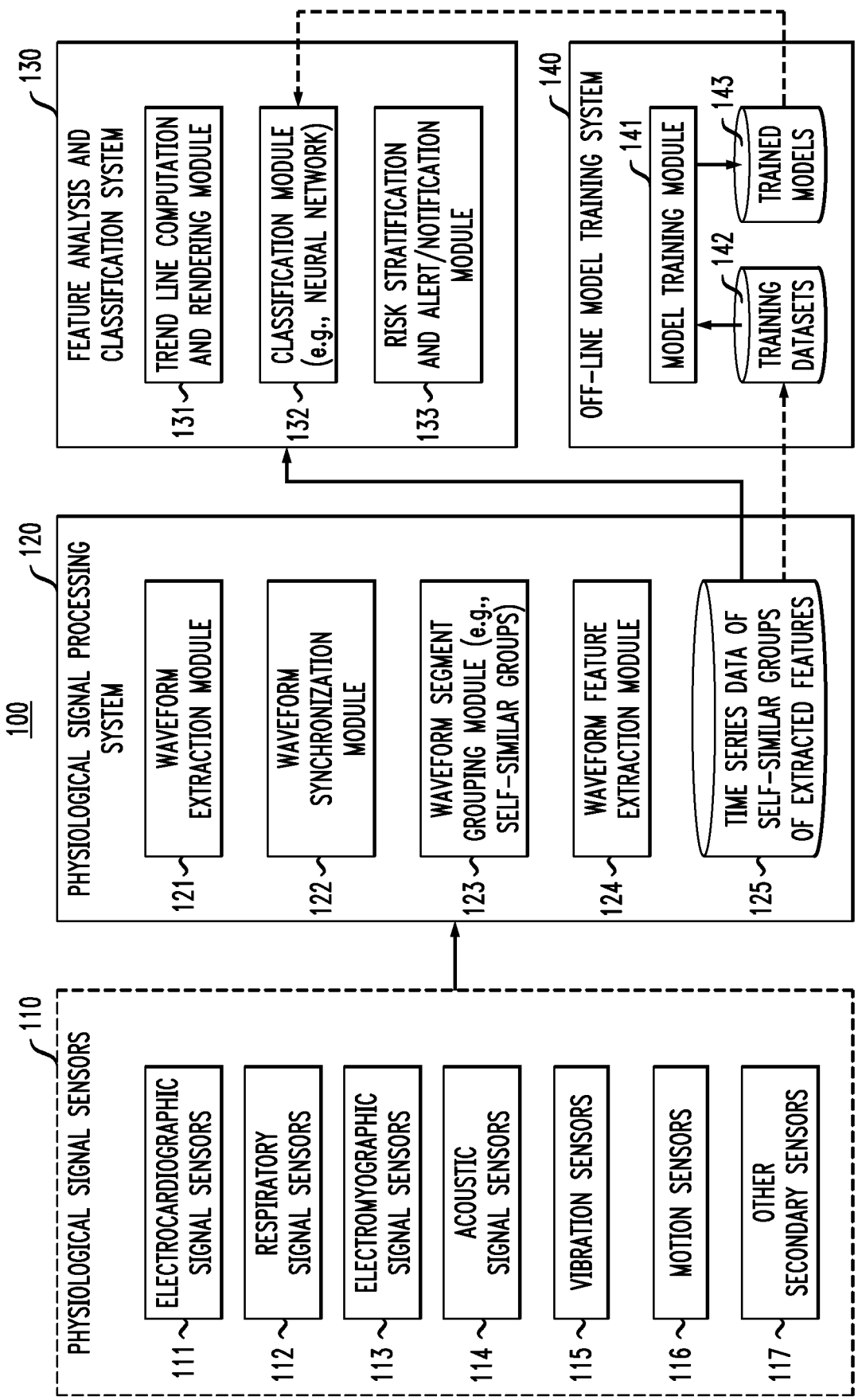
FIG. 1 schematically illustrates a system for monitoring and processing physiological signals, according to an exemplary embodiment of the disclosure.

FIG. 1 schematically illustrates a system 100 for monitoring and processing physiological signals, according to an exemplary embodiment of the disclosure. The system 100 comprises a plurality of physiological signal sensors 110, a physiological signal processing system 120, a feature analysis and classification system 130, and an off-line model training system 140. The physiological signal sensors 110 comprise one or more of electrocardiographic (ECG) signal sensors 111 to detect electrical signals of a heart, respiratory signal sensors 112, electromyographic (EMG) signal sensors 113 (e.g., to sense cardiac muscle electromyographic signals), acoustic signal sensors 114, vibration sensors 115, motion sensors 116, and other secondary sensors 117.

The physiological signal processing system 120 comprises a waveform extraction module 121, a waveform synchronization module 122, and a waveform segment grouping module 123, a waveform feature extraction module 124, and a data store 125 to persistently store time series datasets of self-similar groups of extracted features. The feature analysis and classification system 130 comprises a trend line computation and rendering module 131, a classification module 132, and a risk stratification and alert/notification module 133. The off-line model training system 140 comprises a model training module 141, a data store comprising one or more training datasets 142, and a data store comprising one or more trained models 143. The data stores 142 and 143 can include databases, data repositories, etc., to persistently store the training datasets and models in a persistent storage system.

In general, the system 100 can be implemented to monitor the function of an anatomical feature (e.g., cardiac function) of an individual before, during, and/or after a medical procedure that is performed on the anatomical feature. The system 100 is configured to monitor and collect physiological data from the individual and process the collected physiological data to detect or otherwise identify early signs in the processed physiological data that the individual may possibly or will likely experience dysfunction or complications of the anatomical feature in the future, thereby allowing early action to be taken. For purposes of illustration, exemplary embodiments of the disclosure will be discussed in the context of monitoring and processing physiological signals to detect and predict for possible dysfunction of an anatomical feature (e.g., heart) following a medical procedure (e.g., structural heart intervention, and ablation procedure, placement of a shunt, placement of a filter, etc.).

In this regard, in some embodiments, the plurality of physiological signal sensors 110 are configured to monitor physiological signals from an individual that has undergone a medical procedure such as a structural heart procedure. The physiological signal processing system 120 is configured to analyze the physiological signals and extract features from the physiological signals which are indicative of a function of the anatomical feature following the medical procedure on the anatomical feature. The feature analysis and classification system 130 is configured to analyze the extracted features and predict a risk of the individual developing a post-procedural dysfunction of the anatomical feature as a result of the medical procedure on the anatomical feature (e.g., electrical heart abnormalities such as blocks, arrhythmias, post procedural complications, and other potentially dangerous cardiac issues).

In some embodiments, the plurality of physiological signal sensors 110 comprises one or more body worn or implantable devices that are configured to capture physiological signals from within the body. In some embodiments, the physiological signal sensors 110 comprise one or more body worn sensor devices and/or sensor patches that are coupled to an individual's skin, and which implement the signal processing techniques as disclosed in U.S. National Stage patent application Ser. No. 14/764,830, filed on Jul. 30, 2015, entitled "MODULAR PHYSIOLOGIC MONITORING SYSTEMS, KITS, AND METHODS," which is now U.S. Pat. No. 10,285,617, and U.S. patent application Ser. No. 14/815,251, filed on Jul. 31, 2015, entitled MODULAR PHYSIOLOGIC MONITORING SYSTEMS, KITS, AND METHODS," which are both commonly owned and fully incorporated herein by reference. Exemplary embodiments of such body worn sensor devices and/or sensor patches, and associated signal processing techniques will be discussed below in conjunction with FIGS. 8 and 9.

In some embodiments, the physiological signal sensors 110 are organized into primary sensors and secondary sensors depending on the anatomical feature(s) to be monitored. In particular, the primary sensors are utilized to collect physiological signals that are directly indicative of the functionality of the anatomical feature being monitored. As explained in further detail below, the secondary physiological signal sensors may be used to collect physiological data that can be used, for example, to increase a confidence level that the data collected by the primary sensors is accurate, and to segment a monitoring period into times where the primary sensors can be reliably analyzed, or where one or more trend lines can be more reliably generated from the physiological data acquired using the primary physiological signal sensors.

For example, in the context of monitoring cardiac function, the electrocardiographic signal sensors 111 serve as primary physiological signal sensors to monitor the electrical activity of an individual's heart. As is known in the art, an electrocardiogram records depolarization and repolarization events of various components of the human heart (e.g., atria and ventricles). An electrocardiogram waveform comprises an electrical signal (in millivolts) which represents electrical activity of an individual's heart over time. The electrocardiogram waveform illustrates various features that are indicative of intracardiac conduction, wherein the features comprise, e.g., P-waves, QRS-waves (or QRS complex), T-waves, U-waves, PR intervals, PR segments, QRS duration, ST segments, QT intervals, R-R intervals, etc.

Moreover, in the context of monitoring cardiac function, the physiological signal sensors 112, 113, 114, 115, 116, and 117 can serve as secondary physiological signal sensors to collect secondary physiological data concurrently with the primary electrocardiographic signal data collected by the electrocardiographic signal sensors 111. In some embodiments, the secondary physiological data is correlated with the primary electrocardiographic signal data and utilized to facilitate processing of the primary electrocardiographic signal data to better detect for the presence or possible development of cardiac dysfunction.

For example, in some embodiments, the respiratory signal sensors 112 are configured to monitor one or more aspects of a respiratory rhythm (or respiratory cycle) of an individual in independent ways. For example, the respiratory signal sensors 112 may include one or more of a bioimpedance sensor, a precision movement sensor, a breath sensor, or sensors to detect one or more repeating variations in an ECG waveform amplitude, a QRS complex amplitude, a heart rate variability, a diaphragmatic effort, a diaphragmatic electromyogram, a torso stretch sensor, an electromagnetic sensor, a slowly adapting (pulmonary stretch) receptors (SAR) sensor, oxygen saturation cyclic variation, etc.

The electromyographic signal sensors 113 are configured to record electrical activity produced by skeletal muscles, wherein the electrical activity is recorded to generate an electromyogram (EMG). The EMG data captured by the electromyographic signal sensors 113 can be utilized to determine muscle activity of an individual during a monitoring period, which can include such activity as diaphragmatic activity, muscle exertion, fatigue, etc. Such information may be valuable to determine other bodily functions such as respiration, bladder control, uterine contractions, esophageal function, gastrointestinal function and the like. Such information may be used as secondary physiological data, and in some cases primary physiologic data in the context of this disclosure. In some cases, EMG and ECG data may be simultaneously obtained from the same electrodes on the subject. In some cases, the simultaneous presence of the EMG may adversely affect the nature of the primary physiological data (ECG data) that is collected during the monitoring period. For example, excessive muscle activity that is detected at a given period of time may actually corrupt cardiac cycle information that is captured by an ECG at the given period of time. In this instance, the corrupted cardiac information that is captured during the given period of time can be discarded and not utilized for analysis of heart functionality.

Alternatively, the signals may be simultaneously recorded with a high level of fidelity. For example, in one non-limiting embodiment, the sample rate of the collected signal may be increased if the presence of a strong EMG is detected, and digital filters can be applied to separate the ECG information and the EMG information from the recorded signal such that the primary signal may be used in an analysis. An exemplary scenario is, e.g., collecting ECG data during a stress test or during a test that involves considerable activity, such that nearby EMG signals from the subject may be difficult to eliminate during the recording session.

The acoustic signal sensors 114 are be utilized to capture acoustic signals that emanate from within the body of the individual being monitored. The captured acoustic signals can be utilized to generate a phonocardiogram (or PCG). For example, the acoustic signal sensors 114 can capture audible heart sounds that are generated by the heart during each cardiac cycle. In particular, audible heart sounds include sounds that are generated by the closing of the atrioventricular valves during ventricular contraction, and sounds that are generated by the closing of the semilunar valves during ventricular diastole. Other heart sounds that can be detected include the sound of blood flow into the atria, blood sloshing back and forth in a ventricle, turbulent blood flow (murmur), etc. Other types of phonograms may be obtained by one or more sensors placed onto a subject, including respiratory phonograms, gastrointestinal phonograms, airway obstruction detection, etc.

In addition, the acoustic signal sensors 114 can be utilized to detect instances of when there can be corruption of captured physiological data (e.g., corruption of ECG data, respiratory cycle data, etc.) as a result of the individual speaking, coughing, etc. In this instance, the corrupted physiological data that is captured during a given period of time when the individual is talking, coughing, etc., can be discarded and not utilized for analysis of heart functionality.

The vibration sensors 115 can be utilized to capture vibrations or movements that are indicative of heart motion of an individual being monitored. One or more vibration sensors (or movement sensors) can be configured to capture the cardiac movement from the torso of an individual being monitored. In some embodiments, the vibration sensors 115 comprise accelerometer sensor devices that can be bonded to the skin of the individual to detect vibrations caused by cardiac movement (e.g., valve closures, ventricular movements, etc.). More specifically, cardiac movement comprises one or more of a ventricular movement, an atrial movement, a left-heart contraction, a right-heart contraction, a left-heart expansion, a right-heart expansion, and a valve closure such as an aortic valve closure, a mitral valve closure, a tricuspid valve closure, a pulmonic valve closure, etc. In some embodiments, the vibration data collected by the vibration sensors 115 can be utilized to generate a ballistocardiograph (BCG), which comprises a graphical representation of repetitive motions of the human body due to pressure exerted on surface portions of the body arising from the sudden ejection of blood into blood vessels with each cardiac cycle.

The motion sensors 116 can be utilized to capture body motion such as torso motion and position. For example, torso motion sensors (or torso position sensors) can be located in a region of the sternum (e.g., central region of sternum) of an individual being monitored. The torso position sensors are configured to detect torso angle, torso rotation, and torso rock. In particular, the torso position sensors are utilized to determine torso orientation with respect to the local gravitational vector, torso elastic deformation which is dependent on posture (sitting, laying down, standing), twisting of the torso due to extension of an arm, change in the torso due to bending of the spine, etc. The position of an individual's heart within the chest cavity can change with different torso positions (e.g., standing, laying down, leaning forward, backward, side to side, laying on one side, on the other side, on the back, on the front, in a fetal position, etc.). In this regard, during ECG monitoring of an individual, the relative position of the ECG electrodes with respect to the heart will change as a person's torso position changes. As explained in further detail below, to allow the feature analysis to be as consistent as possible throughout a cardiac cycle waveform comparison and analysis process, the torso position data that is concurrently collected with the ECG data is used to enable a comparison of ECG data of cardiac cycles that are captured at a same or similar torso position. Information related to posture may also be derived from the characteristic changes in the ECG data when compared against simultaneously obtained respiration data.

The additional secondary sensors 117 include other types of physiological signal sensors to obtain secondary physiological data which can be used to augment or otherwise enhance the accuracy of the analysis of the primary physiological data (e.g., ECG data). For example, in some embodiments, the additional secondary sensors 117 include sensors for sensing cardiovascular, hemodynamic, and pulmonary data signals. By way of specific example, one or more additional secondary sensors 117 can be utilized to capture stroke volume (or cardiac output). The stroke volume refers to an amount of blood that is pumped by the left ventricle of the heart in one contraction. The stroke volume does not encompass all the blood contained in the left ventricle, as only about two-thirds of the blood in the ventricle is expelled with each heartbeat (e.g., each cardiac cycle). Together with the heart rate, the stroke volume determines the output of blood by the heart per minute (i.e., cardiac output). Stroke volume on a beat-by-beat basis may be obtained simultaneously with the ECG signal so as to determine the mechanical responses to the electrical activity of the heart.

In some embodiments, the physiological signal processing system 120 is configured to analyze the physiological signals that are captured by one or more of the physiological signal sensors 110 and extract features from the physiological signals which are indicative of cardiac functions of an individual. In particular, the waveform extraction module 121 implements methods that are configured to filter the physiological signals captured by the sensors 110 and generate waveform representations or graphical representations of the captured physiological signals as a function of time. For example, in some embodiments, the waveform extraction module 121 is configured to generate an ECG waveform, a graphical representation of a respiratory cycle waveform, as function of time, a BCG waveform, an EMG waveform, a phonogram, a phonocardiogram, etc.

The waveform synchronization module 122 implements methods that are configured to synchronize the different waveforms generated by the waveform extraction module 121. For example, the waveform synchronization module 122 can time-synchronize an ECG waveform and a respiratory cycle waveform which are concurrently captured. By way of further example, the waveform synchronization module 122 can synchronize an ECG waveform with times of detected changes in torso position of an individual being monitored. Moreover, during a monitoring period, changes in the cardiac cycle can occur over time for various other reasons including, but not limited to, an individual's daily circadian rhythms, and stressors such as autonomic stressors, changes in posture, moving from a lying position to sitting or standing, sitting to standing, rolling over while lying down, etc., a burst in activity level, a strenuous activity, jumping, walking, walking up or down stairs, etc. In this regard, the cardiac cycles of a given individual that are captured over a monitoring period can be grouped into self-similar groups of cardiac cycles based on times when the individual is sleeping, awake, eating, sitting, walking, etc. In addition, the cardiac cycles of a given individual that are captured over a monitor period can be grouped into self-similar groups of cardiac cycles based on the individual's activity level, heart rate, autonomic stress reactivity, etc.

The waveform segment grouping module 123 is configured to group primary physiological data into self-similar groups based on, e.g., secondary physiological data which is captured concurrently with the primary physiological data. For example, in the context of monitoring cardiac function and, in particular, intracardiac conduction, the cardiac cycles that are recorded in ECG signals can be segmented into self-similar groups of cardiac cycles. As a specific example, the cardiac cycles within a given self-similar group comprise ECG segments of cardiac cycles that are captured, for example, at a same phase of a respiratory cycle of the individual (e.g., inhalation phase), at a same torso position of the individual (e.g., laying down), etc.

In this regard, the secondary physiological data that is captured using the secondary physiological signal sensors can be used to increase the confidence level of the quality or validity of the primary physiological data collected by the primary physiological signal sensors, by allowing the monitoring period to be segmented into times where the primary physiological data can be reliably analyzed, or where one or more trend lines can be more reliably generated from the primary physiological data. Indeed, the process of grouping the physiological data captured from one or more sensors into associated temporal periods during the overall monitoring period, facilitates a comparison with population trend lines. The process of organizing the data into self-similar groups, enhances the ability to extract, analyze, and compare miniature wavelets, micro-features or other miniature characteristics of a particular feature in the physiologic signal and thereby detect/identify small changes and fluctuations in the given feature over time.

When an individual breaths, moves, flexes muscles, and changes his/her posture during a monitoring session, the heart position in the torso of the individual will change with respect to the location of the monitoring electrodes on the torso. This presents a complication in terms of assessing the micro-feature changes that may be occurring in the heart during the monitoring session. By simultaneously monitoring the respiratory rhythm of the individual (rhythm meaning rate, depth, cadence, duty cycle, inspiration rates, etc.), along with the precision postural changes of the subject, the torso of the subject, or more particularly the orientation of the electrode array positioned upon the torso of the subject, a correlation between the heart position and particular cardiac beats of the electrocardiogram can be established. These are the beats where the electrode positioning with respect to the heart are as repeatable as possible. Then, comparing beat by beat within these groupings, it is possible to track the small changes in the waveforms that may ultimately transform into an arrhythmia, block, or other complication.

In one non-limiting embodiment, the sensors may include a plurality of postural sensors that are configured to determine a gravitational vector with respect to one or more electrodes coupled thereto on the torso of the subject. In such cases, the plurality of postural sensors may be used to construct a more accurate topographical mapping of the placement of electrodes on the torso of the subject at any given time. This can be particularly advantageous for individuals that are heavy set, where tissue folds and creases may be formed during certain postural orientations (e.g. such as laying on one's side, etc.). Such a mapping enables a more accurate modeling of the electrode positional changes from heartbeat to heartbeat and, thus, a more precise determination of self-similar groups of features of cardiac cycles.

The waveform feature extraction module 124 is configured to extract features from the physiological waveforms of the physiological signals, wherein the extracted features are indicative of a function of the anatomical feature (e.g., heart) that is being monitored following a medical procedure on the anatomical feature. For example, in some embodiments, the waveform feature extraction module 124 is configured to extract a plurality of features indicative of intracardiac conduction over a plurality of cardiac cycles, wherein the plurality of extracted features comprise one or more of (i) waveform features comprising one or more of P-waves, T-waves, QRS-waves, U-waves, R-R intervals, PR timing intervals, QT timing intervals, QRS timing intervals, ST segments, and PR segments and (ii) morphological features of the waveform features. Further, in some embodiments, the morphological features that are extracted comprise one or more of waveform shape, waveform contour, waveform amplitude, waveform width, waveform phase, waveform polarity, a notch, a local inversion, a ripple, an amplitude change, relative timing or polarity inversion thereof, a perturbation, a repetitive perturbation, a low amplitude, high frequency wavelet, a wavelet that repeats along with essentially a same period as a parent waveform, etc.

The extracted waveform features are output from the waveform feature extraction module 124 and persistently stored in the data store 125 as time series datasets that are associated with self-similar groups of extracted features. The time series datasets 125 are processed by the feature analysis and classification system 130. The feature analysis and classification system 130 is configured to analyze the extracted features and predict a risk of an individual developing a dysfunction of an anatomical feature (e.g., heart).

The trend line computation and rendering module 131 implements methods that are configured to compute a trend line for a given extracted feature of the plurality of extracted features based on the time series data 125 associated with the given extracted feature. The feature analysis and classification system 130 comprises a display system, wherein the trend line computation and rendering module 131 is configured to render and display the time series data and the computed trend line for the given extracted feature on the display.

As is known in the art, a trend line is a line that is used to represent the behavior of a set of data to determine if there is a certain pattern. A trend line may comprise a straight line (positive slope, negative slope, zero slope) based on a first-order linear function, or a curved line based on a higher-order function or non-linear function, which indicates a general pattern or direction of time series data (information in sequence over time) for a given extracted feature. A trend line may be computed based on the values of the time series data using statistical techniques such as exponential smoothing or moving averages. A trend line is an analytical tool which is typically utilized in conjunction with a scatter plot (a two-dimensional graph of ordered pairs) to determine if there is a relationship between two variables and to determine or infer conclusions regarding the behavior of the time series data and/or make predictions.

The risk stratification and alert/notification module 133 implements methods that are configured to compare a computed trend line for the time series data of a given extracted feature with known trend lines for the given extracted feature as determined from a cohort patient population, and risk stratify the computed trend line based on a result of comparing of the computed trend line with the known trend lines. The risk stratification and alert/notification module 133 is configured to risk stratify the computed trend line into one of a plurality of zones comprising a low risk zone, an increasing risk zone, and a high risk zone, and generate an alert or notification when the extracted feature is determined to enter into a high risk zone.

In some embodiments, the classification module 132 is configured to process the time series data 125 of a given extracted feature using a trained model 143 (e.g., a trained neural network) which is trained to classify a risk profile of the given extracted feature based on processing results of the time series data applied to the, e.g., trained neural network model. The output of the classification module 132 provides a prediction of a risk level of the individual developing an anatomical dysfunction (e.g., cardiac dysfunction). The model training module 141 of the off-line model training system 140 implements known methods for training neural network models for the extracted features using the training dataset 142 of time series data of extracted waveform features obtained from the cohort patient population. As illustrated in FIG. 1, the training datasets 142 can be periodically updated with additional time series data of extracted features which are acquired during a current monitoring period of an individual. In some embodiments, the model training module 141 is configured to train models that are utilized by the risk stratification module 133 to perform risk stratification by comparing determined trends in changes of extracted waveform features of individuals being monitored to known trends in changes of the extracted waveform features from the cohort patient population.

In some embodiments, a neural network can be trained holistically on an entire signal or cardiac cycles that are recorded for a given individual, and utilized to predict a risk or likelihood that the individual will develop cardiac dysfunction. The neural network may be reasonably deep enough such that key underlying features are being analyzed and trained anyway, even if such features are relatively small compared to the overall signal or the overall self-similar beats, i.e., the feature extraction step is really extracting the cycles that are to be compared within a group, such as all cycles happening at a particular posture during full exhale, etc. One may also see a trend in the secondary data, such as a change in respiratory depth over time that would be subtle when observed momentarily, but change significantly in the lead up to an emergency event, etc.

It is to be appreciated that the system 100 utilizes high-fidelity electrocardiographic signal sensors 111 from which the output, either alone or when integrated with other physiological data captured by one or more secondary sensors, allows the system 100 to detect, sense, and provide predictive value for future onset of cardiac dysfunction (e.g., heart blocks, arrhythmias, or complications of any sort). The rhythms that may be evaluated by the system 100 include complete heart block and other conduction abnormalities as a result of structural heart procedures such as valve replacement, transcutaneous valve replacement, aortic valve replacement, transcutaneous aortic valve replacement (TAVR), etc. The system 100 allows for the maintenance of normal conduction from the syncytium of normal cardiac microfiber/His-Purkinje fibers function. This includes the normal initiation patterns and maintenance of sinus rhythm. The system 100 can detect for the presence or onset of cardiac dysfunctions such as atrial fibrillation, atrial tachycardias, ventricular arrhythmias including simple and complex ectopy up to and including ventricular tachycardia and ventricular fibrillation. The system 100 is configured to detect normal function events that may be interrupted by electrical or mechanical pressures due to structural heart interventions To facilitate an understanding of the exemplary systems and methods as discussed herein, a brief description will now be provided with regard to the anatomy and functionality of a human heart. The heart wall of a human consists of three layers: epicardium, myocardium and endocardium. The epicardium is the outermost layer of the heart wall which serves to lubricate and protect the outside of the heart. The myocardium is the thick muscular middle layer of the heart wall which comprises the cardiac muscle tissue that is responsible for pumping blood. The endocardium layer is a thin layer below the myocardium which lines the inside of the heart and serves to prevent blood from sticking to the inside walls of the heart and forming blood clots.

The human heart comprises four chambers: the right atrium, the left atrium, the right ventricle and the left ventricle. The atria are connected to veins that carry blood to the heart and thus act as receiving chambers for blood. The ventricles are connected to arteries that carry blood away from the heart, wherein the ventricles serve as pumping chambers that pump blood out of the heart. The chambers on the right side of the heart form part of a circulatory loop that maintains pulmonary circulation to the lungs, while the chambers on the left side of the heart form part of a circulatory loop that pumps blood to the extremities of the body in the systemic circulatory loop.

The atria of the heart have a relatively thin myocardium layer as the atria serve to pump blood to the ventricles, while the ventricles of the heart have a relatively thick myocardium layer to pump blood to the lungs or throughout the entire body. The human heart comprises valves that prevent blood from flowing backwards into the heart. The valves include atrioventricular valves and semilunar valves. The atrioventricular (AV) valves are located in the middle of the heart between the atria and ventricles and only allow blood to flow from the atria into the ventricles. The AV valve on the right side of the heart is called the tricuspid valve and the AV valve on the left side of the heart is called the mitral valve (or bicuspid valve). The AV valves are attached on the ventricular walls and held in place by strings called chordae tendineae. The chordae tendineae pull on the AV valves to keep them from folding backwards and allowing blood to regurgitate past them.

The semilunar valves are located between the ventricles and the arteries that carry blood away from the heart. The semilunar valve on the right side of the heart is the pulmonary valve which prevents the backflow of blood from the pulmonary trunk into the right ventricle. The semilunar valve on the left side of the heart is the aortic valve which prevents the aorta from regurgitating blood back into the left ventricle.

The conduction system of the heart controls the cardiac cycles (heartbeat rhythm) by generating and transmitting electrical signals through the structures of the heart. Heart muscle cells include normal contractile cells which are specialized for contraction and conduction, while other heart muscle cells are specialized for conduction only. In particular, the conduction system of the heart comprises the sinoatrial (SA) node (conduction only), atria muscle (contraction and conduction), the atrioventricular (AV) node (conduction only), AV bundle, i.e., bundle of His (conduction only), left and right bundle branches (conduction only), Purkinje fibers (conduction only), and ventricular muscle (contraction and conduction).

The SA node comprises a bundle of cells located in the wall of the right atrium, and comprises the sinus pacemaker (i.e., the heart pacemaker). The SA node is responsible for controlling the pace of the heart (i.e. sinus rhythm) and generates an electric signal which starts the cardiac cycle and causes the atria to contract. The electric signal generated by the SA node travels along the wall (through the muscle) of the atria.

The AV node comprises a mass of conductive tissue located in the right atrium. The AV node receives an electrical signal transmitted from the SA node. The AV node serves as an electrical pathway that connects the atria and the ventricles (wherein in a normal heart, the atria and ventricles are electrically insulated) so that electrical impulses in the atria can travel to the ventricles. The AV node transmits the electrical signal to the AV bundle (bundle of His) which then forks into the left bundle branch and the right bundle branch. The Purkinje fibers branch off from the left and right bundle branches. The Purkinje fibers transmit the electrical signal to the walls of the ventricles, thereby stimulating the cardiac muscle cells of the ventricles to contract in a coordinated manner to pump blood out of the heart. The His-Purkinje System (HPS) is responsible for the rapid electric conduction in the ventricles. It relays electrical impulses from the AV node to the muscle cells and, thus, coordinates the contraction of ventricles in order to ensure a proper cardiac pumping function.

The cardiac cycle refers to the performance of the human heart from the beginning of one heartbeat to the beginning of the next heartbeat, i.e., through one contraction and relaxation of both the atria and ventricles. A contraction event (of either the atria or ventricles) is referred to as systole, and a relaxation event is referred to as diastole. A single cardiac cycle consists of two periods: a first period in which the heart muscle relaxes and refills with blood (i.e., diastole), followed by a second period of contraction and pumping of blood (i.e., systole). The electrical activity in the human heart is detectable by an ECG. The ECG records depolarization and repolarization of the atria and ventricles. As is known in the art, depolarization occurs when heart cells (e.g., myocardial cells) receive an electrical impulse. During depolarization, a heart cell undergoes a change in electrical charge distribution which results in less negative charge inside the cell. Repolarization is the process by which a heart cell is recharged to a resting potential. An ECG detects electrical activity with respect to depolarization of the atria, depolarization of the ventricles, and repolarization of the ventricles.

Figure 2:
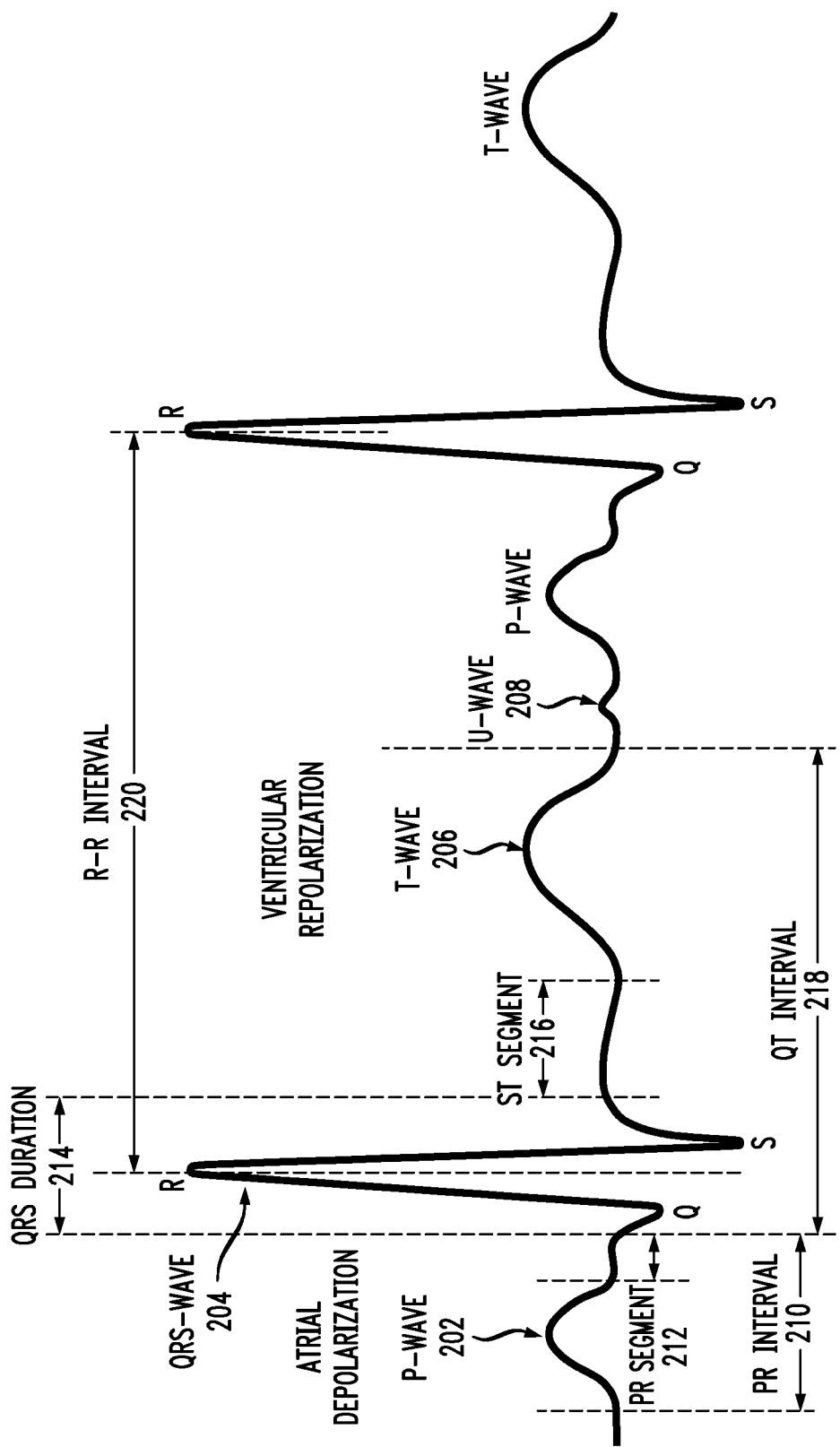
FIG. 2 illustrates an electrocardiogram waveform comprising cardiac cycles of a human heart.

FIG. 2 illustrates an electrocardiogram waveform 200 comprising cardiac cycles of a human heart. The electrocardiogram waveform 200 comprises an electrical signal (in millivolts) that captures electrical activity of the heart over time. The electrocardiogram waveform 200 comprises a P-wave 202, a QRS-wave 204 (alternatively referred to as a QRS complex), a T-wave 206, and a U-wave 208, which are generated for each cardiac cycle. The electrocardiogram waveform 200 shows depolarization which occurs in the four chambers of the heart. The P-wave 202 corresponds to atrial contraction. The QRS-wave 204 corresponds to the contraction of the ventricles. The QRS-wave 204 is relatively larger (in amplitude) than the P-wave 202 due to the relative difference in muscle mass of the atria and ventricles, which masks the relaxation of the atria. The T-wave 206 corresponds to the relaxation of the ventricles.

In particular, the SA node initiates depolarization in the right atrium and the left atrium, which causes contraction of the atria (atrial systole), and results in generation of the P-wave 202 on the electrocardiogram signal. The SA node sends the depolarization wave to the AV node which, after a delay of about 100 ms to allow the completion of the atrial contraction, causes contraction (systole) of the right and left ventricles, and generation of the QRS-wave 204. The completion of the P-wave 202 represents the end of the ventricular diastole and the start of the ventricular systole. The contractions (systole) of the ventricles start at the Q-wave of the QRS complex 204. During contraction of the ventricles, the right and left atriums repolarized and relax. The right and left ventricles are then repolarized and relaxed, which results in generation of the T-wave 206 (which corresponds to the repolarization of the AV node and the bundle branches). The U-wave 208, which is generated after the T-wave 206, represents, inter alia, repolarization of the Purkinje Fibers.

Each electrode placed on the torso of a subject is positioned within a different spatial site of the three-dimensional electric field generated by the heart during function. Thus, each electrode or electrode pair can be used to assess the heart from a different perspective. Small changes in the characteristics of neighboring electrodes on the torso may be used to extract features of the cardiac activity or signals from regions of the heart which would otherwise have been masked by other waveforms generated by the cardiac tissues during their function.

In one non-limiting embodiment, a plurality of electrodes situated on the torso of the subject may be used to enhance the above feature extraction. A collective signal may be generated from the plurality of electrodes, and/or individual differences in signals obtained from particular electrodes may be utilized to generate features for further analysis. In particular, when combined with local orientation sensors, as described above, signals may be selectively extracted from the collective array subject to the immediate positioning of a particular electrode or electrode pair with respect to the heart at a given point in time.

As further shown in FIG. 2, the electrocardiogram waveform 200 comprises additional features that can be extracted and analyzed using techniques as disclosed herein to assess cardiac function. For example, FIG. 2 illustrates a PR interval 210, a PR segment 212, a QRS duration 214, a ST segment 216, a QT interval 218, and an RR interval 220. In electrocardiography, the PR interval is the period (in milliseconds) that extends from the beginning of the P-wave (i.e., the onset of atrial depolarization) to the beginning of the QRS-wave (i.e., the onset of ventricular depolarization). The PR interval 210 is analyzed to determine whether the impulse conduction from the atria to the ventricles is normal or abnormal. In other words, the PR interval 210 corresponds to the conduction delay of the atrial impulses through the AV node to the ventricles (wherein the delay allows for the atria to fill the ventricles with blood before the ventricles begin to contract). The PR interval 210 is typically between 120 milliseconds and 200 milliseconds. A prolonged PR interval (e.g., greater than 220 milliseconds) is indicative of a first-degree AV block. A shortened PR interval (e.g., less than 120 milliseconds) is indicative of an accessory pathway between the atria and ventricles which allows the atrial impulses to bypass the AV node. As noted above, in a normal heart, the atrial myocardium and the ventricular myocardium are electrically insulated from each other by fibrous rings. However, certain heart abnormalities result in additional connections between the atria and the ventricles which enable the atrial impulses to bypass the AV node and cause pre-excitation of the ventricles.

The PR segment 212 comprises the flat line segment between the end of the P-wave 202 and the beginning of the QRS-wave. The PR segment 212 is utilized as a reference line of the ECG signal such that the amplitude of the waves/deflections of the ECG signal is measured relative to the PR segment 212.

The QRS duration 214 (or QRS interval) corresponds to the time period of ventricular depolarization. In clinical practice, a normal duration 214 of the QRS complex 204 is deemed to be between 80 milliseconds and 100 milliseconds. When the QRS duration 214 is between 100 milliseconds and 120 milliseconds, it is deemed to be slightly prolonged. When the QRS duration 214 is greater than 120 milliseconds, it is deemed to be abnormal. A widening of the QRS complex 214 is indicative of a decreased spread of ventricular depolarization, either due to disease of the His-Purkinje network and/or reliance on slower, muscle-to-muscle spread of depolarization. The QRS duration 214 increases when it takes longer for electrical activity to travel throughout the ventricular myocardium. The normal conduction of an electrical impulse through the AV node to the ventricles via the His-Purkinje system results in a normal QRS duration. When electrical activity does not properly conduct through the His-Purkinje system, but instead travels from myocyte to myocyte, a longer time is necessary, and the QRS duration is widened. A widened QRS duration is indicative a cardiac dysfunction such as a right bundle branch block, a left bundle branch block, non-specific intraventricular conduction delay, ventricular arrhythmias such as ventricular tachycardia, pre-excitation of the ventricles due to accessory pathways, etc. It is to be noted that in some embodiments, the term QS-timing interval (or QS interval) as used herein denotes a time between the beginning of the QRS complex and the beginning of the systolic wave.

In electrocardiography, the ST segment 216 connects the QRS complex and the T-wave 206 and has a duration of 5 milliseconds to 150 milliseconds. It starts at the J point (junction between the QRS complex 204 and the ST segment 216) and ends at the beginning of the T-wave 206. In other words, the ST segment 216 is the flat, isoelectric section of the ECG waveform between the end of the S wave (the J point) and the beginning of the T-wave 206, which reflects a period of zero potential between ventricular depolarization and repolarization. The ST segment represents the interval between ventricular depolarization and repolarization. The most important causes of ST segment abnormality (elevation or depression) is myocardial ischemia or myocardial infarction. The nature of the ST segment 216 (elevated, depressed, slope, etc.) is indicative of other heart abnormalities including, but not limited to, left and right bundle branch blocks, etc.

The QT interval 218 is measured from the beginning of the QRS-wave 204 and the end of the T-wave 206. The QT interval 218 represents the time of ventricular activity including both depolarization and repolarization. In practice, a normal QT interval is deemed to be 0.36 seconds to 0.44 seconds. Since the QT interval 218 depends primarily on heart rate (QT interval increases with slower heart rate and decreases with higher heart rate), it is typically reported as a corrected QT interval (QTc), a value normalized for a heart rate of 60 bpm. Long QT syndrome is a heart rhythm disorder in which heart muscle takes longer than normal to recharge between beats, which can cause serious irregular heart rhythms (arrhythmias).

The R-R interval 220 represents the time between two consecutive R waves in the electrocardiogram waveform 200. The R-R interval 220 represents the time for one complete cardiac cycle. The R-R interval 220 is utilized to assess the ventricular rate. The heart rate (HR) is a reciprocal of the R-R interval 220. It is to be understood that the electrocardiogram waveform 200 of FIG. 2 is a schematic illustration that is presented for illustrative and explanatory purposes. In this regard, it is to be understood that in practice, one or more of the waves of the electrocardiogram waveform 200 could differ in size, shape, amplitude, duration, and/or timing, etc.

Figure 3:
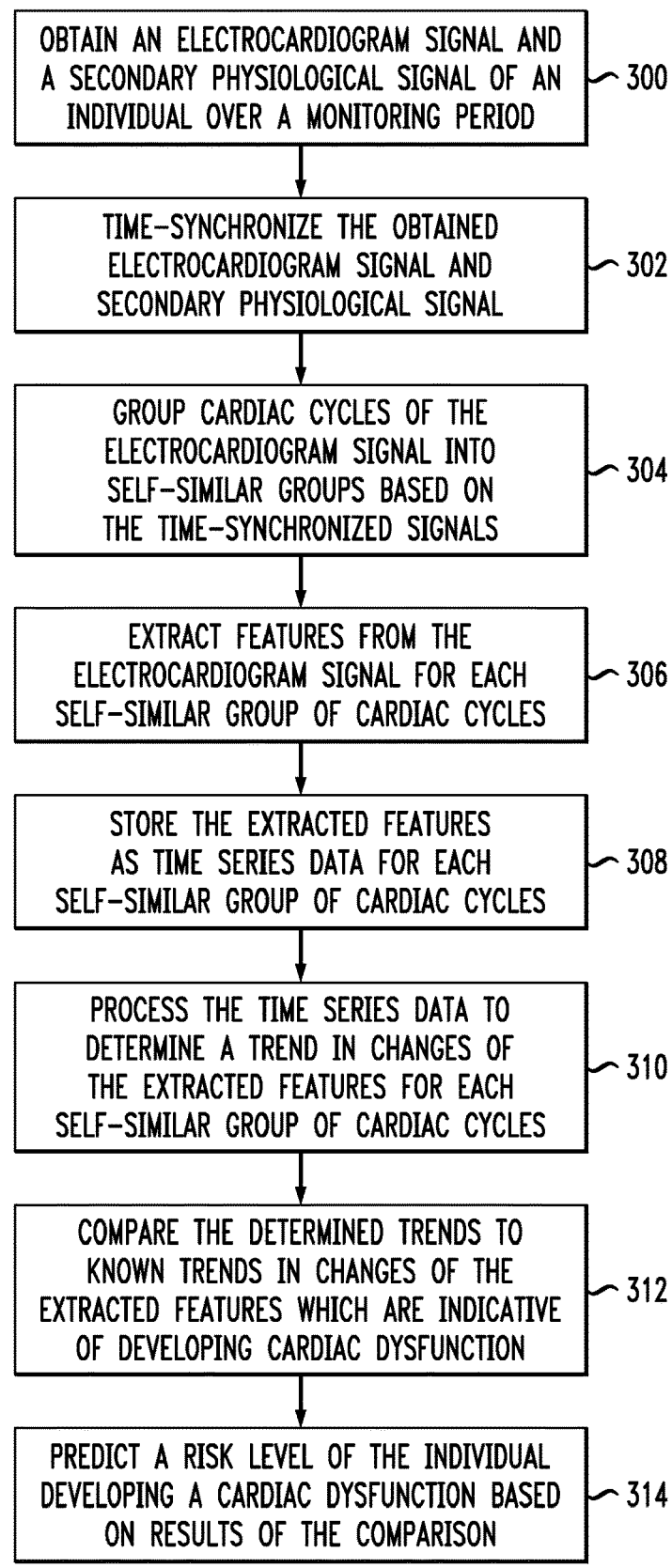
FIG. 3 is a flow diagram which illustrates a method for monitoring and processing physiological signals, according to an exemplary embodiment of the disclosure.

FIG. 3 is a flow diagram which illustrates a method for monitoring and processing physiological signals according to an exemplary embodiment of the disclosure. For illustrative purposes, the flow diagram of FIG. 3 will be discussed in the context of the system 100 of FIG. 1, wherein FIG. 3 illustrates operational modes of the system of FIG. 1. In addition, for illustrative purposes, the flow diagram of FIG. 3 will be discussed in the context of processing electrocardiogram signals as a primary signal, and one or more secondary signals, to detect and predict for possible cardiac dysfunction of an individual.

An initial phase comprises obtaining an electrocardiogram signal and a secondary physiological signal of an individual over a monitoring period (block 300). Depending on the clinical application, the monitoring period may be one or more of (i) pre-procedure, (ii) intra-procedure and (iii) post procedure. For pre-procedure applications, the system 100 of FIG. 1 can be utilized prior to a cardiac procedure to establish a baseline assessment of the cardiac conduction and rhythmic systems, which baseline data is then persisted and utilized for comparison with newly acquired data at a subsequent time either during or after a therapeutic procedure has been accomplished.

For intra-procedure applications, the system 100 of FIG. 1 can be utilized during a cardiac procedure to guide the procedure, providing an indication of completion of the procedure, and/or provide an indication of safety or conversely warn of potential and possibly imminent problems or complications that will result from the procedure, etc. The system 100 can be utilized to predict an occurrence of one or more problems that may or will arise during the procedure or in a post procedure recovery time period.

In another embodiment, the system 100 of FIG. 1 is utilized post-procedure (e.g., after completion of a structural heart procedure) to monitor, analyze, notify, store, display and predict adverse cardiac events that have occurred or are likely to occur as a result of the cardiac procedure. In some embodiments, a target monitoring period post-procedure is one of: (i) less than an hour, (ii) about an hour, (iii) multiple hours, (iv) about a day, (v) multiple days, (vi) about a week, and (viii) multiple weeks, and wherein the monitoring and processing of physiological signals can be continuous or intermittent during the target monitoring period. For example, in some embodiments, the monitoring period can be 1 day per week for an entire year. The monitoring period will vary depending on various factors such as the type of anatomical function being monitored and assessed, and the purpose for monitoring, etc.

The electrocardiogram signals that are captured during the monitoring period are time-synchronized with the one or more secondary physiological signals that are concurrently captured with the electrocardiogram signals during the monitoring period (block 302). For example, in the system 100 of FIG. 1, the waveform extraction module 121 will process the physiological signals that are captured by the sensors 110 and generate waveform representations or graphical representations of the captured physiological signals as a function of time (e.g., generate an ECG, a graphical representation of a respiratory cycle as function of time, BCG, a EMG, a phonogram, a phonocardiogram, etc.). The waveform synchronization module 122 will time-synchronize the different waveforms generated by the waveform extraction module 121. The time-synchronization allows the system 100 to group cardiac cycles (i.e., heartbeat waveform segments) of the electrocardiogram signal into self-similar groups of cardiac cycles (block 304). In some embodiments, the grouping of the cardiac cycles is performed by the waveform segment grouping module 123 of FIG. 1.

As noted above, the system 100 may implement a plurality of sensor devices to concurrently collect electrocardiogram signals along with data from secondary sensors that are configured to acquire cardiovascular, hemodynamic, and pulmonary, as well as secondary signal data from secondary sensors such as precision motion sensors, respiratory sensors, etc. As further noted above, as an individual breathes, moves, flexes muscles, and changes posture during the monitoring period, the position of the heart in the torso changes with respect to the location of the ECG electrodes on the torso. This raises a challenge with respect to assessing the micro-feature changes that may be occurring in the electrical activity (e.g., intracardiac conduction) of the heart during the monitoring session. By simultaneously monitoring the respiratory rhythm of the subject (e.g., respiration rate, depth, cadence, duty cycle, inspiration rate, etc.), along with precision postural changes of the subject, a correlation can be established between the heart position and particular cardiac cycles of the electrocardiogram. These are the cardiac cycles where the electrode positioning with respect to the heart are as repeatable as possible. In this manner, the waveform segments of the cardiac cycles of the electrocardiogram signal can be organized into self-similar groups based on the collected data from the one or more secondary sensors.

Furthermore, as noted above, the data collected from secondary sensors such as activity sensors, electromyographic sensors, acoustic sensors, etc., may be utilized to determine whether to accept or discard certain cardiac cycles from the analysis due to excessive movement, excessive nearby muscle activity, and/or excessive audible corruption of the respiration cycle (such as due to the subject speaking, coughing, etc.).

In other embodiments, the waveform segments of cardiac cycles may be organized in a hierarchical manner—first by the acceptance of cardiac signals that are time-synchronized to data from secondary sensors (such as movement, EMG, and/or acoustic signals that fall below predefined thresholds), and then organized based on the time-varying relative position of the electrodes with respect to the heart, for example, via a combination of postural information, based on changes in torso elastic deformation and respiratory cycle. The grouping of the cardiac cycles into self-similar groups allows feature extraction, feature analysis and predictions to be performed for self-similar cardiac cycles within a given group, with a high-level of precision.

In particular, once the cardiac cycles are grouped into self-similar groups, various waveform features can be extracted from the waveform segments of the electrocardiogram signal for some or all of the self-similar groups of cardiac cycles (block 306). It is to be noted that depending on the length of the monitoring period, each self-similar group of cardiac cycles can have thousands of cardiac cycle waveform segments that are extracted from an electrocardiogram signal of an individual that is captured over days, weeks, etc., of the given monitoring period. As noted above, in some embodiments, the physiological signal processing system 120 of FIG. 1 is configured to analyze the electrocardiogram signal and extract a plurality of features indicative of intracardiac conduction over a plurality of cardiac cycles within a given self-similar group of cardiac cycles. Such extracted features comprise one or more of (i) waveform features comprising one or more of P-waves, T-waves, QRS-waves, U-waves, R-R intervals, PR timing intervals, QT timing intervals, QRS timing intervals, ST segments, and PR segments and (ii) morphological features of the waveform features. The morphological features that can be extracted from the waveform features of a given self-similar group of cardiac cycles include, but are not limited to, waveform shape, waveform contour, waveform amplitude, waveform width (in terms of time), waveform phase, waveform polarity, a notch, a local inversion, a ripple, an amplitude change, relative timing or polarity inversion thereof, a perturbation, a repetitive perturbation, a low amplitude, high frequency wavelet, a wavelet that repeats along with essentially a same period as a parent waveform. In this regard, the features that are extracted include, but are not limited to, micro-morphological characteristics and high frequency/low amplitude characteristics of P-waves, T-waves, and/or QRS-waves, and other features which enable assessment of one or more intracardiac conduction events including His bundle-Purkinje fiber transmission events, intra atrial conduction events, intraventricular conduction events, or a combination thereof.

In some embodiments, the extracted features associated with each self-similar group of cardiac cycles are stored as time series datasets (block 308) which are processed to identify trends in the time series data set that may be indicative of, e.g., normal cardiac function or cardiac dysfunction. For example, in some embodiments, the time series datasets associated with features that are determined over multiple cardiac cycles within a given self-similar group of cardiac cycles include, but are not limited to, (i) timing data with regard to R-R intervals, PR intervals (normalized to R-R interval and/or non-normalized), QS intervals (normalized to R-R interval and/or non-normalized), QS intervals, QT intervals, timing delay between onset of P-wave and valve closure, etc., and (ii) changes in waveform characteristics over time, including, but not limited to, QRS-wave amplitude, QRS-wave width, etc.

The time series dataset for each self-similar group of cardiac cycles are processed to determine trends in changes of the extracted features for each self-similar group (block 310). The determined trends are then compared to known trends in changes of the extracted features which are indicative of developing cardiac dysfunction (block 312). Based on the results of the comparison, a risk level is predicted with respect to the likelihood of the individual developing a cardiac dysfunction (block 314). The comparison and/or risk predictive algorithms may be trained from a cohort population data set, recorded from similar subjects in similar environments and after similar medical procedures. The comparison and risk predictive algorithms may then be implemented on new test cases to stratify risk during the monitoring period so as to predict the likelihood that an individual (being monitored) may develop a cardiac disorder or dysfunction, such as arrhythmia, heart block, or other conduction-related disorders or complications that can arise following a cardiac procedure.

Figure 4B:
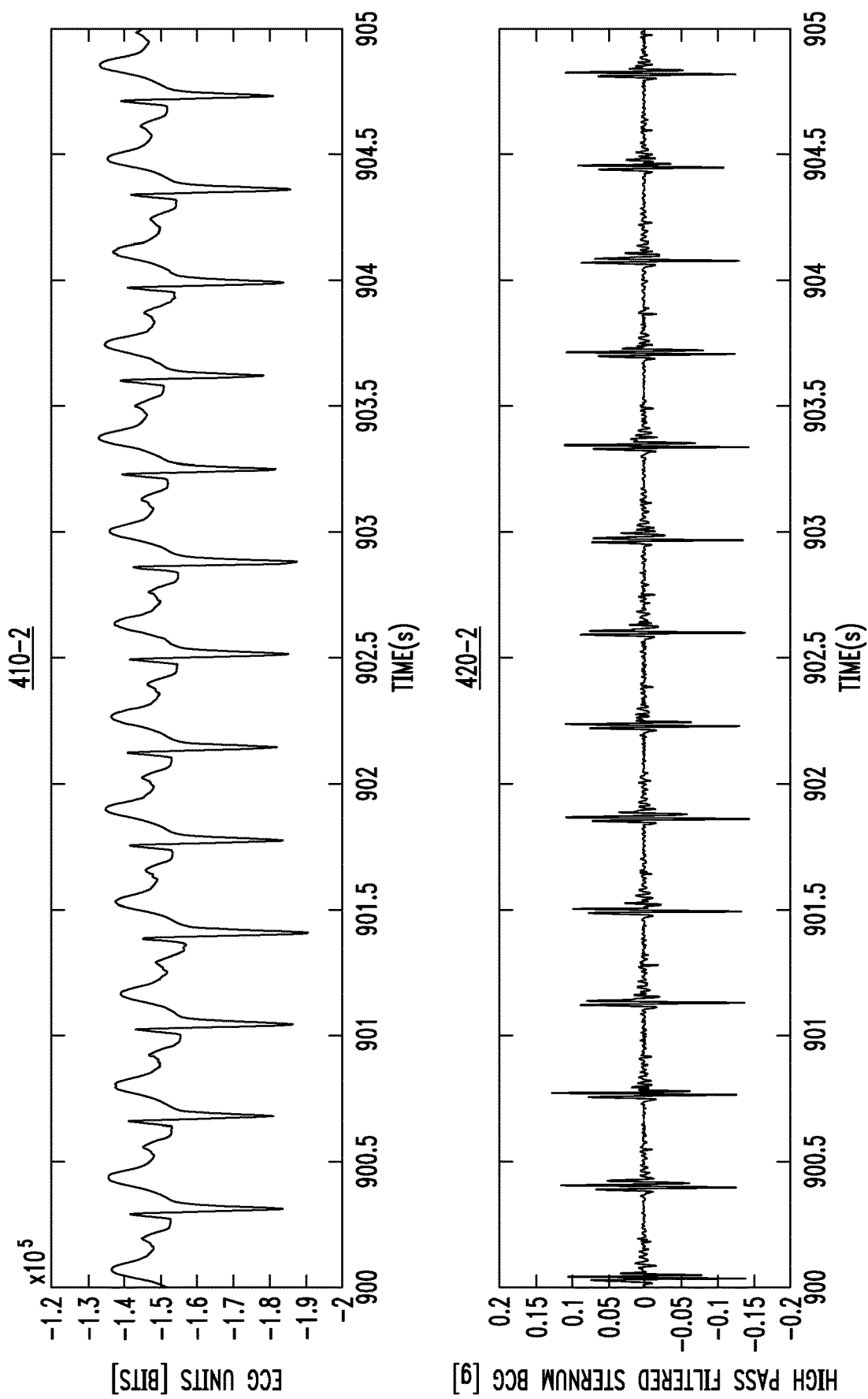

FIGS. 4A, 4B and 4C schematically illustrate a method for time-synchronizing a primary physiological signal waveform with a secondary physiological signal waveform, according to an exemplary embodiment of the disclosure. FIGS. 4A-4C schematically illustrate a mode of operation of the waveform synchronization module 122 of FIG. 1 and the time-synchronization process 302 in FIG. 3. In particular, FIG. 4A illustrates an ECG waveform 410-1 and a high-pass filtered BCG waveform 420-1, which show time correlated heart valve movements and ECG signals from a site on a torso of an individual. The waveforms 410-1 and 420-1 were captured using electrodes that were positioned on a sternum of the individual with the electrodes horizontally spaced about 2 inches apart, and using sensors configured to capture electrical activity of the heart and sensors (e.g., accelerometers) to capture vibrations associated with heart valve closure events. The waveforms 410-1 and 420-1 in FIG. 4A were captured in a state in which the individual was standing before physical activity. The BCG waveform 420-1 illustrates a series of aortic valve movements 422 and mitral valve movements 424 that were captured in synchronization with the cardiac cycles in the ECG waveform 410-1.

FIG. 4B illustrates an ECG waveform 410-2 and a high-pass filtered BCG waveform 420-2, which show time correlated heart valve movements and ECG signals from the same site on the torso of an individual while laying down just after physical activity. FIG. 4B shows that various characteristics of the waveforms (e.g., time delay, amplitude, waveform shape, and additional waves, etc.) can change and morph over time as a result of a physical exercise stressors. In particular, FIG. 4B shows that following an exercise stressor, the ECG and BCG signal waveforms 410-2 and 420-2 have changed dramatically (as compared to the ECG and BCG signal waveforms 410-1 and 420-1 of FIG. 4A), where the individual's heart rate is elevated, the amplitudes of the valve closure events are significantly increased, and where T-wave and P-wave morphology as well as the QRS complex have changed dramatically.

FIG. 4C illustrates an ECG signal waveform 410-3 and a high-pass filtered BCG signal waveform 420-3, which show time correlated heart valve movements and ECG signals from the same site on the torso of an individual while laying down about 4 minutes after the physical activity stressor. FIGS. 4A-4C demonstrate that changes in various features of ECG and BCG signals may manifest themselves during stressors, and tracing such features during recovery can highlight overall health of the heart organ and the conduction therein.

Figure 5:
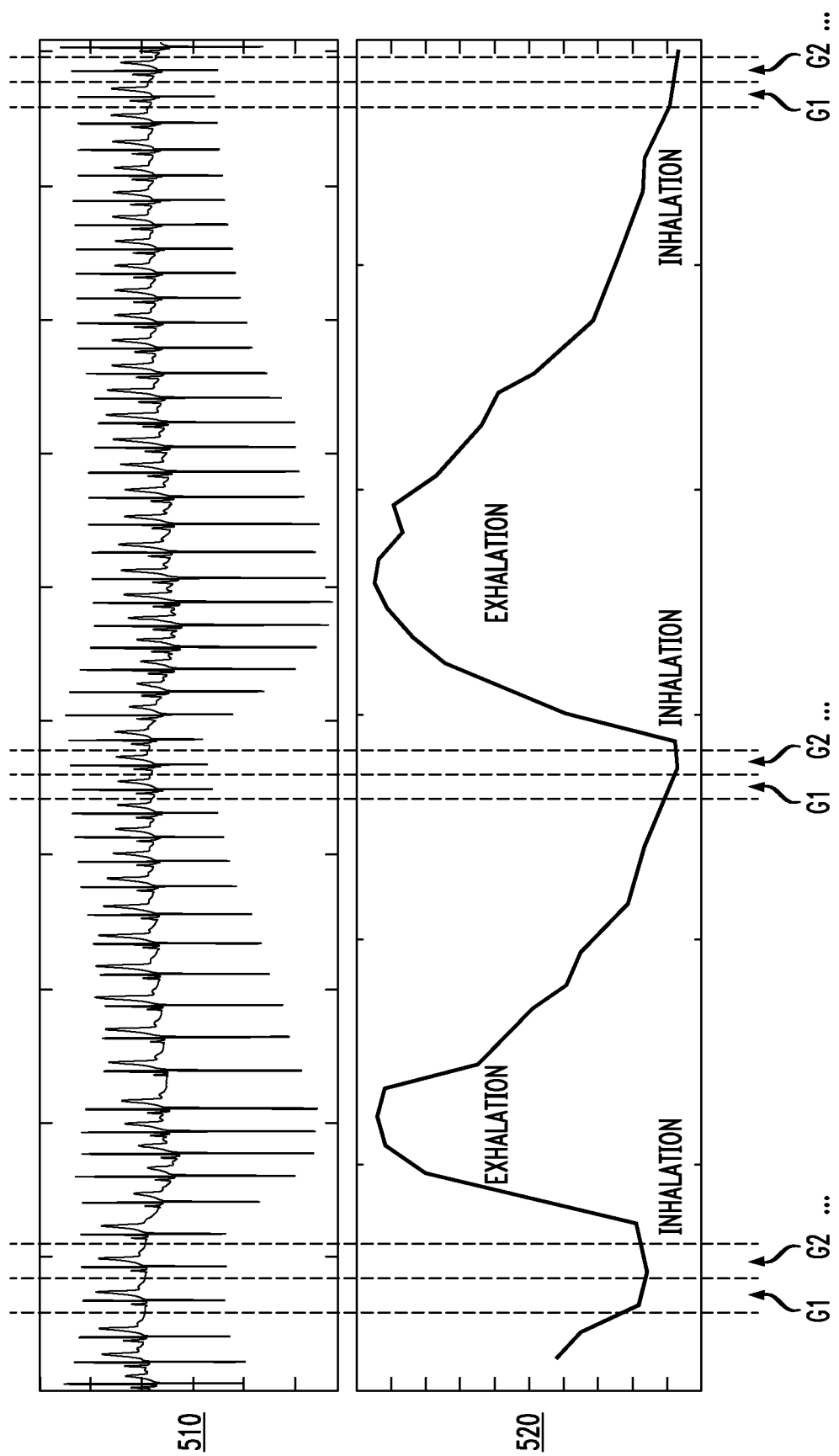
FIG. 5 schematically illustrates a method for time-synchronizing a primary physiological signal waveform and a secondary physiological signal waveform and grouping segments of the primary physiological signal waveform into self-similar groups, according to an exemplary embodiment of the disclosure.

FIG. 5 schematically illustrates a method for time-synchronizing a primary physiological signal waveform with a secondary physiological signal waveform and grouping segments of the primary physiological signal waveform into self-similar groups, according to an exemplary embodiment of the disclosure. FIG. 5 schematically illustrate a mode of operation of the waveform synchronization module 122 and waveform segment grouping module 123 of FIG. 1 and the time-synchronization process 302 and waveform segment grouping process 304 in FIG. 3.

In particular, FIG. 5 illustrates an ECG signal waveform 510 and a respiration signal waveform 520, which are time-synchronized. FIG. 5 illustrates raw data of the respiration signal waveform 520 which is captured over several respiration cycles from a seated position with moderately changing posture throughout the recording. As shown in FIG. 5, the amplitude of the ECG signal waveform 510 is modulated as a result of the respiration cycle 520 due to changes in the relative position of the ECG electrodes and the heart due to inhaling and exhaling. In addition, FIG. 5 schematically illustrates a process of grouping cardiac cycles from the same points in the respiratory cycle into self-similar groups, G1, G2, . . . , which allows precise comparison and analysis of extracted features of cardiac data within the self-similar groups. In particular, in the exemplary embodiment of FIG. 5, each group G1 and G2 will include a plurality of cardiac cycles (heartbeat segments) that fall within the same or similar phase of the inhalation stage of the respiratory cycle. In the exemplary embodiment of FIG. 5, while only two groups G1 and G2 are shown for ease of illustration, other self-similar groups of cardiac cycles can be maintained for cardiac cycles that fall within the same phases of the inhalation and exhalation stages of the respiratory cycle 520.

Figure 6:
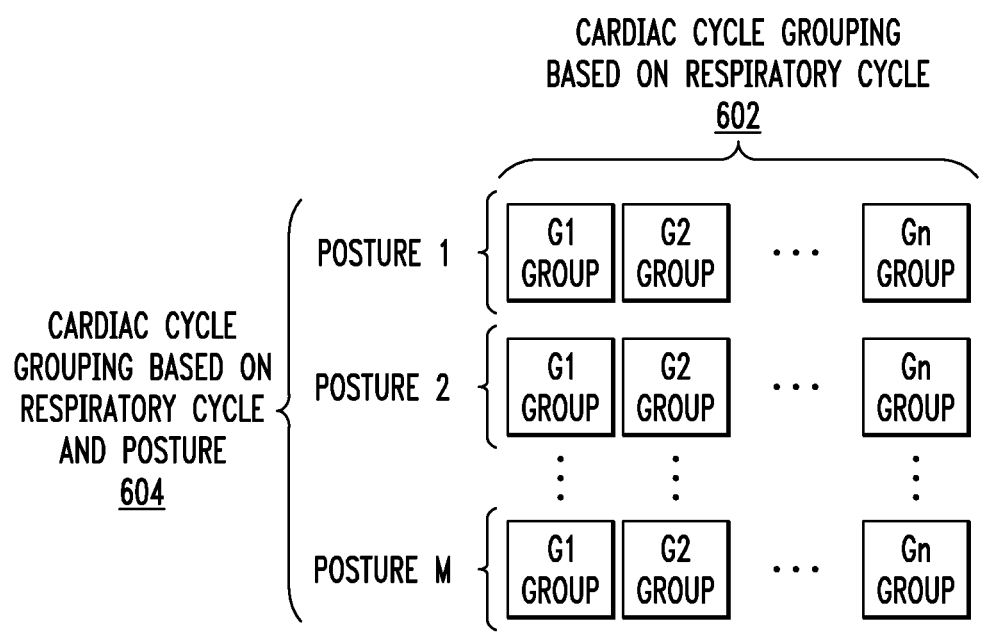
FIG. 6 schematically illustrates a process of grouping segments of a primary physiological waveform signal into self-similar groups based on multiple secondary signals, according to an exemplary embodiment of the disclosure.

FIG. 6 schematically illustrates a process 600 of grouping segments of a primary physiological waveform signal into self-similar groups based on multiple secondary signals, according to an exemplary embodiment of the disclosure. In particular, FIG. 6 schematically illustrates a process of grouping cardiac cycles into a plurality (n) of self-similar groups G1, G2, . . . Gn, based on secondary data of a respiratory cycle (602), as well as a plurality (m) of self-similar groups based on posture as well as a respiratory cycle (604). In the exemplary embodiment of FIG. 6, the cardiac cycles can be grouped based on changes in postures of an individual which are detected during a monitoring period (e.g., laying down, standing, reclining in a chair, etc.)

Figure 7:
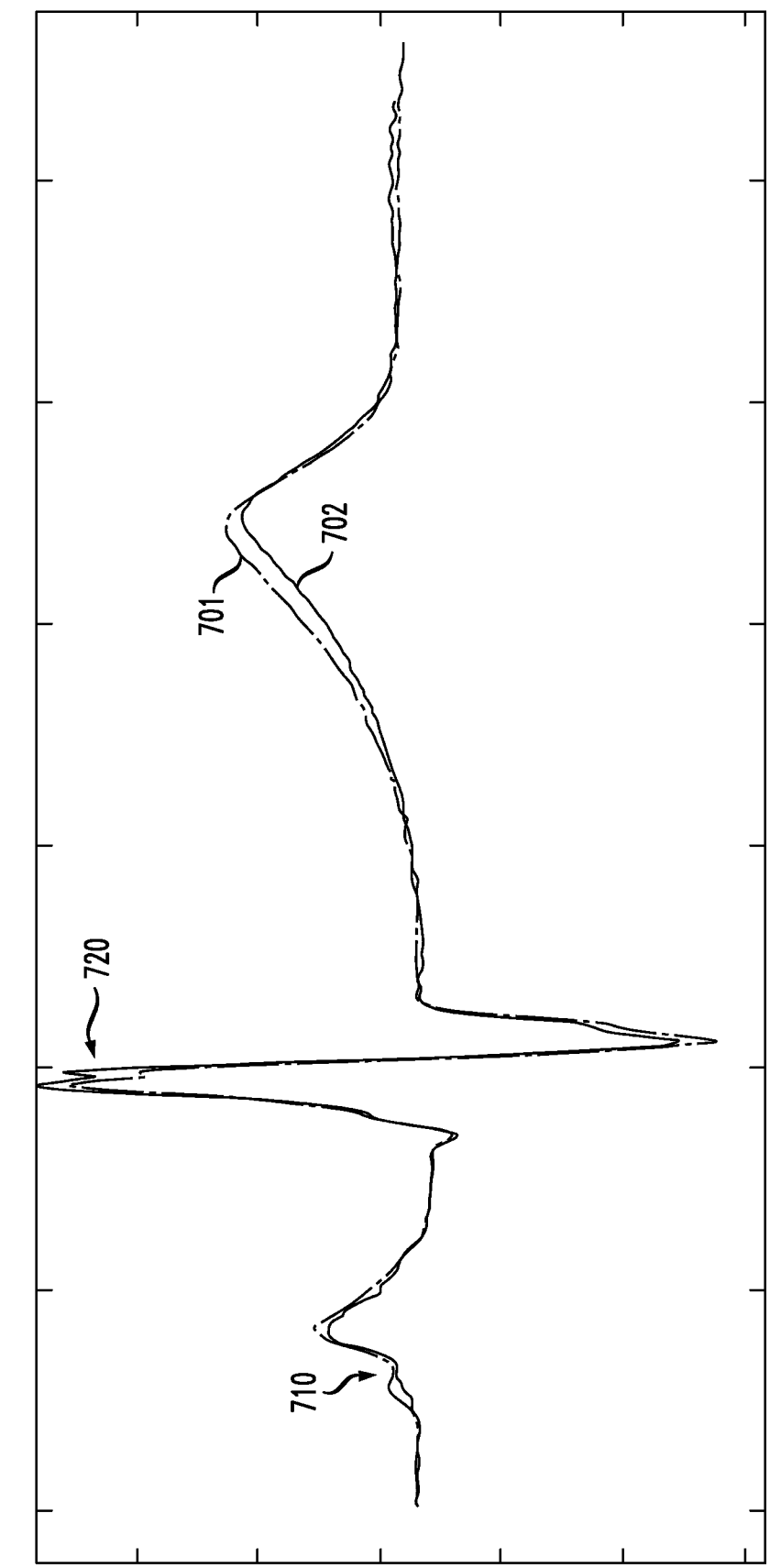
FIG. 7 illustrates a self-similar group of cardiac cycles extracted from a same phase of a respiration cycle over multiple cycles of a respiration rhythm, according to an exemplary embodiment of the disclosure.

FIG. 7 illustrates a self-similar group of cardiac cycles 700 extracted from a same phase of a respiration cycle over multiple cycles of a respiration rhythm, according to an exemplary embodiment of the disclosure. In particular, FIG. 7 illustrates a first cardiac cycle waveform 701 and a second cardiac cycle waveform 702, which are superimposed to illustrate morphological changes in the electrocardiogram waveform segments of such cardiac cycles 701 and 702. FIG. 7 illustrates notches 710 of the P-wave segments of the cardiac cycle waveforms 701 and 702. Such notches 710 may correspond with His-bundle conduction or left or right branch events. In addition, FIG. 7 illustrates high-frequency features 720 in the QRS-wave segments, which may also correspond to conduction differences along the ventricle surfaces and variation in conduction pathways and/or repolarization of the atria, which is usually masked in lower fidelity data.

Further correlation with the valve closures and movements of the heart may correlate with the variation in the conduction pathways. In particular, relating to potential delays between the electrical signal arrival at the cardiac muscle and the resulting contractions and recovery of the muscle, which is mechanically related to the timing of the valve closures, cardiac wall movements, etc. The waveform of the phonograms and precision movements may also demonstrate microfeatures similar to the small variations in the P-waves, T-waves, U-waves, QRS-complexes, etc. Also, as the wave progresses towards a blocked state or an arrhythmia, the features of the waveform may become more unstable, more separate from each other or more apparent in the figures. Such changes may take place over the period of minutes, hours, or days. During such long-term monitoring, the time periods may be segmented as well, such that daily variations are taken into account, as the daily circadian rhythms, as well as over even longer periods of time.

Furthermore, some changes may manifest themselves during stressors. Some non-limiting examples of stressors include, an autonomic stressor, a change in posture, moving from a lying position to sitting or standing, sitting to standing, rolling over while lying down, etc., a burst in activity level, a strenuous activity, jumping, climbing stairs, walking, walking up or down stairs, etc. Such stressors are often more common and natural when the subject is being observed in their own environment. During a monitoring period, the system may be configured to automatically initiate an ultra-high-fidelity monitoring mode when the posture, movement, and other secondary sensors demonstrate that the subject is in the right state for a comparison. A high-fidelity state may include a higher bandwidth, a lower noise floor, a heightened filtering state, etc.

Figure 8:
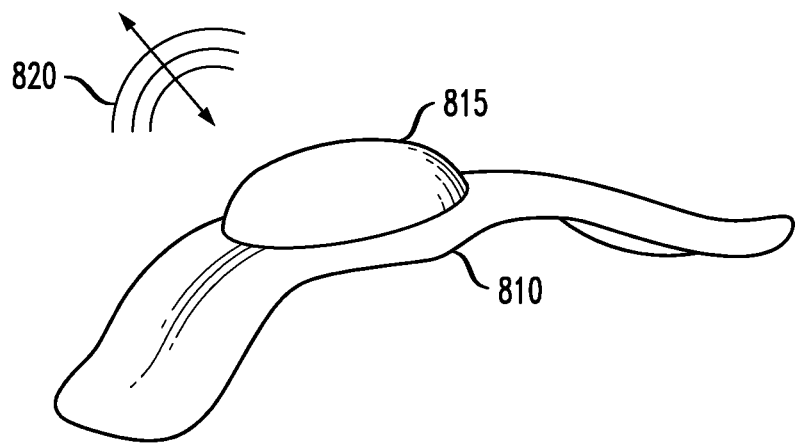
FIG. 8 schematically illustrates a sensor device comprising a sensor patch and a sensor module coupled to the sensor patch, which can be implemented in the system of FIG. 1 to collect physiological data, according to an exemplary embodiment of the disclosure.

As noted above, the physiological sensors 110 may comprise one or more body worn sensor devices and/or sensor patches that are coupled to an individual's skin, and implement signal processing techniques as disclosed in the disclosures of the above-noted U.S. patent application Ser. Nos. 14/764,830 and 14/815,251. These patent disclosures describe various configurations and structures of sensor devices comprising a sensor patch/sensor module pairs, which are designed to capture various types of physiological signals of an individual wearing the sensor devices. For example, FIG. 8 schematically illustrates a sensor device 800 comprising a sensor patch substrate 810 and a sensor module 815 coupled to the sensor patch substrate 810.

The sensor patch substrate 810 is formed from a flexible, elastically deformable, and/or stretchable material. The sensor patch substrate 810 further comprises an adhesive layer, multiple patch interconnects, and multiple electrodes. The sensor patch interconnects and the electrodes are electrically coupled together via one or more conducting traces located on the sensor patch substrate 810 or embedded in the sensor patch substrate 810, etc. The sensor module 815 comprises multiple module interconnects that are configured, dimensioned, and arranged so as to mate with the corresponding patch interconnects of the sensor patch substrate 810. The path interconnects may comprise snap elements, magnetic elements, etc. FIG. 8 shows the sensor module 815 coupled to the sensor patch substrate 810 and having wireless capability to communicate 820 with other sensor modules of other sensor devices or a host system to obtain or transmit physiological data captured by the sensor devices.

Figure 9:
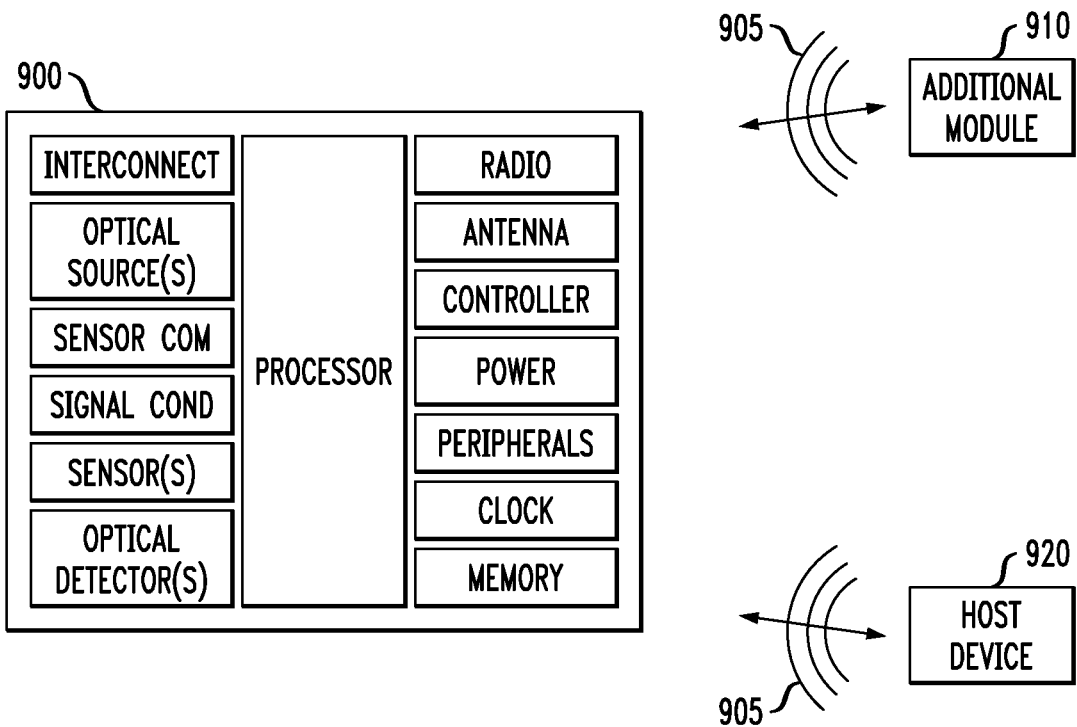
FIG. 9 schematically illustrates various components and functionalities of a sensor module which can be implemented in the sensor device of FIG. 8, according to an exemplary embodiment of the disclosure.

FIG. 9 schematically illustrates various components and functionalities of a sensor module according to exemplary embodiments as disclosed in the above-noted U.S. patent application Ser. Nos. 14/764,830 and 14/815,251. As shown in FIG. 9, a sensor module 900 comprises one or more interconnects, sensors, optical source(s), optical detector(s), a radio frequency (RF) transmitter, an antenna, sensor communication circuitry, signal conditioning circuitry, one or more processors, a memory device, a controller, a power supply, power management circuitry, and/or energy harvesting circuitry, and one or more peripherals. The sensor module 900 is configured to wirelessly communicate 905 with an additional sensor module 910 (e.g. perhaps situated in the same monitoring system, on the same subject, etc.), and a host device 920. In some embodiments, the sensor module 900 is configured to implement the functionalities one or more or all of the various modules of the physiological signal processing system 120 and/or the feature analysis and classification system 130 of FIG. 1.

The dimensions, configurations, functionalities, etc., of the sensor module/sensor patch pair will vary depending on the types of sensors implemented and the types of physiological signals to be captured. For example, a sensor patch/module pair can be equipped with a plurality of electrophysiological sensing electrodes and sensor circuitry configured to collect and process electrophysiological information (e.g., ECG signals, EMG signals, BCG signals, etc.). In addition, a set of two or more sensor patch/module pairs may be configured to collect electrophysiological information synchronously from different locations on the body of the individual.

It is to be appreciated that the wearable sensor devices as disclosed in the above-noted U.S. patent application Ser. Nos. 14/764,830 and 14/815,251 allow for the detection and acquisition of low noise, broadband, and high gain physiological signals. For example, such wearable sensor devices allow for the acquisition of electrocardiogram signals with a bandwidth in a range of about 0.001 Hz to about 8000 Hz. In addition, the wearable sensor devices allow for detection of waveform features in the electrocardiogram signals with a signal to noise ratio in a range of about 3 dB to about 70 dB. In particular, the wearable sensor devices are capable of detecting P-waves and U-waves of electrocardiogram signals with a signal to noise ratio in a range of about 20 dB to 50 dB, which allows features of such waves to be more readily detected, as compared to conventional monitoring technologies. In addition, the wearable sensor devices are capable of capturing electrocardiogram signals with a noise floor of about 3 uV rms or less and, in particular, 1 uV rms or less.

Figure 10:
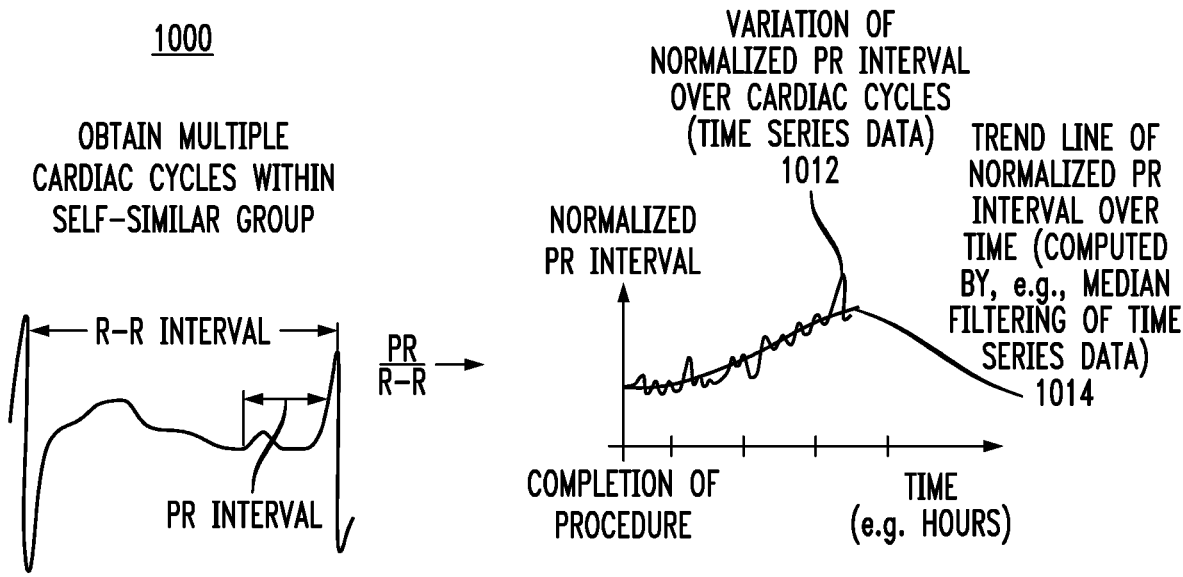
FIG. 10 schematically illustrates a method for extracting and normalizing PR intervals of a plurality of cardiac cycles within a self-similar group of cardiac cycles over time and computing a trend line for the normalized PR interval values, according to an exemplary embodiment of the disclosure.

FIG. 10 schematically illustrates a method for extracting and normalizing PR intervals of a plurality of cardiac cycles within a self-similar group of cardiac cycles over time and computing a trend line for the normalized PR interval values, according to an exemplary embodiment of the disclosure. In particular, FIG. 10 illustrates an ECG waveform 1000 for a given cardiac cycle, in which a PR interval of the given cardiac cycle within the ECG waveform 1000 is extracted and normalized with respect to the R-R interval of the given cardiac cycle. A time series dataset of normalized PR interval values can be determined over time from a plurality of cardiac cycles within self-similar group of cardiac cycles.

FIG. 10 further illustrates a trend line graph 1010 which includes a plot of (i) time series data 1012 of the normalized PR interval values that are determined from multiple cardiac cycles within a self-similar group of cardiac cycles, and (ii) a computed trend line 1014 of the normalized PR interval values. In some embodiments, the trend line 1014 is computed from the time series data 1012 of normalized PR interval values using a median filtering process. As discussed herein, the feature analysis and classification system 130 (FIG. 1) can compare the computed trend line 1014 against known trend lines of normalized PR interval features that are computed from time series data associated with a cohort patient population to thereby determine a risk of the individual developing cardiac dysfunction based on the normalized PR interval trend. For instance, the risk stratification and alert/notification module 133 can be configured to generate an alert if the normalized PR-timing interval is determined to increase by more than 25%, or more than 50%, etc., during a monitoring period, wherein such increase is indicative of an increasing risk for developing cardiac dysfunction.

The method illustrated in FIG. 10 can be applied to other features that are extracted from cardiac cycles of an electrocardiogram of an individual that is monitored over a given period of time following a medical. For example, a QS-timing interval and R-R timing interval can be extracted from each of a plurality of cardiac cycle waveforms within a self-similar group of cardiac cycles. The QS-timing interval for each cardiac cycle can be normalized with respect to the R-R timing interval of that cardiac cycle to thereby generate a time series dataset of normalized QS intervals for each (or at least some) of the self-similar group of cardiac cycles. A trend line can then be determined for a given time series dataset of normalized QS-timing interval, wherein an alert can be generated if the normalized QS-timing interval increases by more than 25%, 50%, etc.

Figure 11:
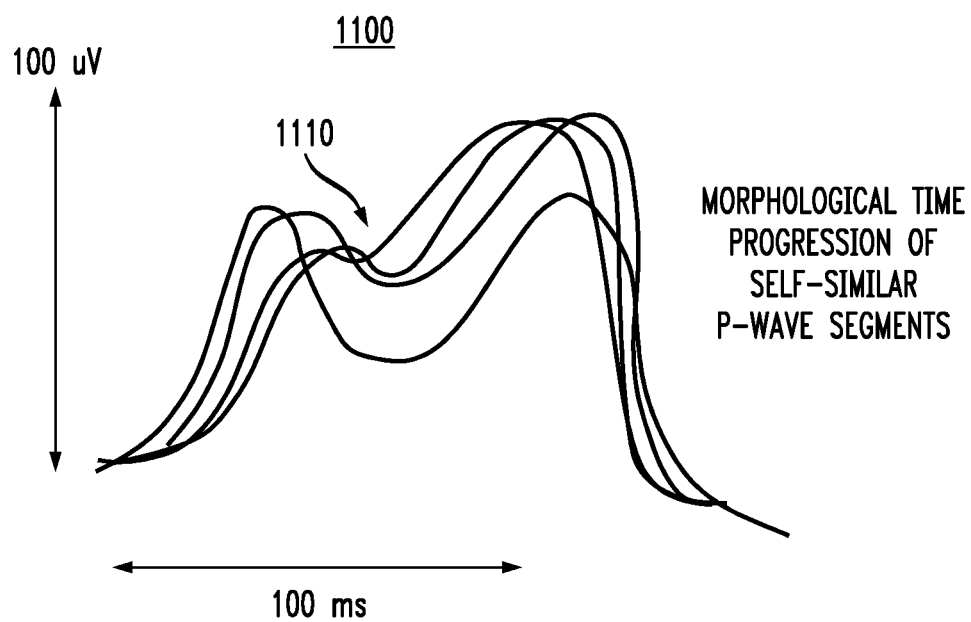
FIG. 11 illustrates a morphological time progression of self-similar P-wave segments that are extracted from a plurality of cardiac cycles within a self-similar group of cardiac cycles over time, according to an exemplary embodiment of the disclosure.

FIG. 11 illustrates a morphological time progression of self-similar P-wave segments that are extracted from a plurality of cardiac cycles within a self-similar group of cardiac cycles over time, according to an exemplary embodiment of the disclosure. In particular, FIG. 11 schematically illustrates a plurality of superimposed P-wave segments 1100 that are extracted from a self-similar group of cardiac cycles of a given individual. FIG. 11 illustrates that various features of the P-wave segments, such as amplitude, shape, etc., can vary over time. A time series dataset that represents the variation of a given feature (e.g., width, amplitude, etc.) of the P-wave segments within the self-similar group of P-wave segments can be utilized to compute a trend line. The computed trend line can be compared against known trend lines for feature variations in P-wave segments associated with a cohort patient population to thereby determine a risk of the individual developing cardiac dysfunction based on the computed trend line for given feature of the P-wave segments.

Indeed, the shape and size of the P-waves can be indicative of normal or abnormal cardiac function. For example, FIG. 11 illustrates the presence of notch features 1110 within the P-wave segments. A notched P-wave or biphasic P-wave can be indicative of an abnormality referred to as left atrial enlargement (LAE). Other heart disorders can lead to an increased duration of the P-wave, or an increased amplitude of the P-wave.

Figure 12:
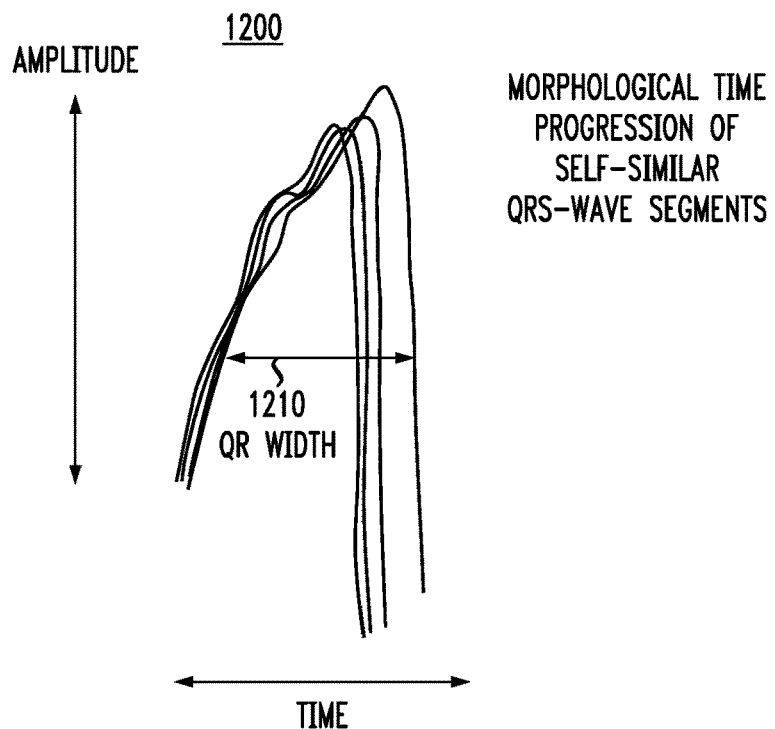
FIG. 12 illustrates a morphological time progression of self-similar QRS-wave segments that are extracted from a plurality of cardiac cycles within a self-similar group of cardiac cycles over time, according to an exemplary embodiment of the disclosure.

FIG. 12 illustrates a morphological time progression of self-similar QRS-wave segments that are extracted from a plurality of cardiac cycles within a self-similar group of cardiac cycles over time, according to an exemplary embodiment of the disclosure. In particular, FIG. 12 schematically illustrates a plurality of superimposed QRS-wave segments 1200 that are extracted from a self-similar group of cardiac cycles of a given individual. FIG. 12 illustrates that various features of the QRS-wave segments, such as amplitude, QR width, etc., can vary over time. A time series dataset that represents the variation of a given feature, such as QR interval 1210, QRS width, etc., of the QRS-wave segments within the self-similar group of QRS-wave segments can be utilized to compute a trend line. The computed trend line can be compared against known trend lines for feature variations in QRS-wave segments associated with a cohort patient population to thereby determine a risk of the individual developing cardiac dysfunction based on the computed trend line for given feature of the P-wave segments. In an electrocardiogram, a QR interval is the period between the onset of the QRS complex and the peak of the R wave. The QR interval is indicative of ventricular activation time, and can be utilized to assess or otherwise predict diastolic dysfunction, left ventricular stiffness, etc.

Figure 13:
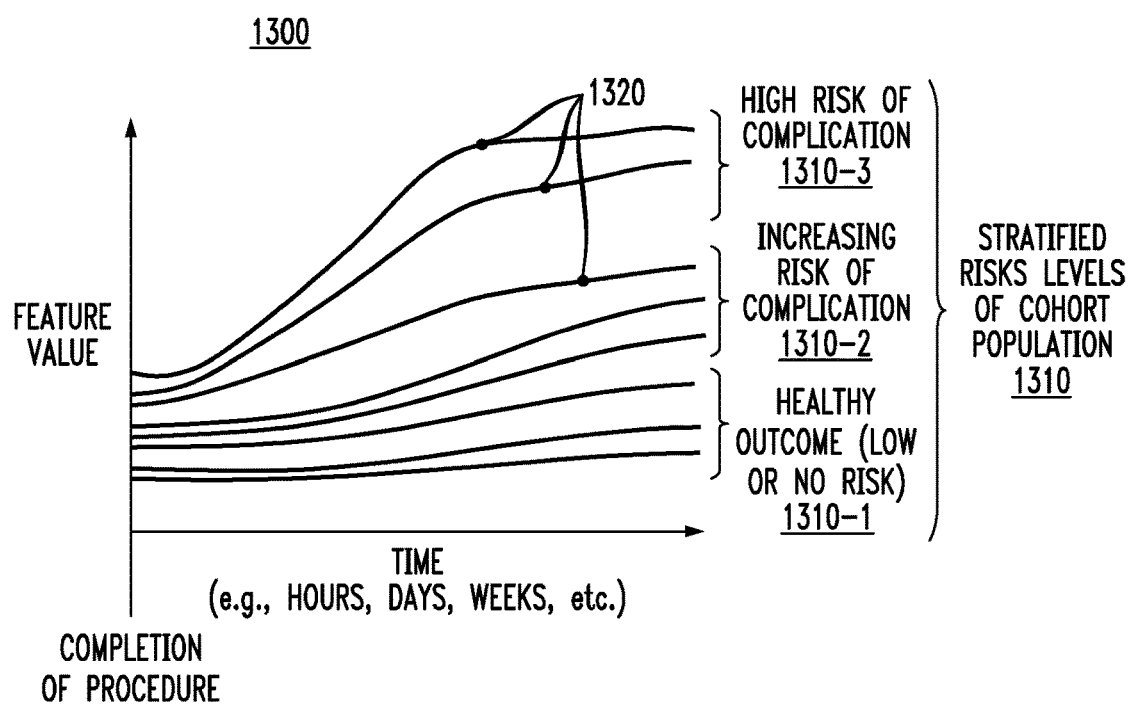
FIG. 13 illustrates a process for risk stratifying a plurality of known trend lines determined from time series data for a given extracted feature associated with a cohort patient population, according to an exemplary embodiment of the disclosure.

FIG. 13 illustrates a process for risk stratifying a plurality of known trend lines determined from time series data for a given extracted feature associated with a cohort patient population, according to an exemplary embodiment of the disclosure. In particular, FIG. 13 generically illustrates a plurality of known trend lines 1300 that are computed from time series data of a given feature value, which are collected from a cohort patient population. FIG. 13 further illustrates stratified risk levels 1310 that are determined from the plurality of trend lines 1300. In particular, the stratified risk levels 1310 include a low or no risk level 1310-1, an increasing risk level 1310-2, and a high-risk level 1310-3.

The trend lines associated with the low risk level 1310-1 represent trend lines of collected time series data from the given feature which resulted in a healthy outcome (no complication) following the completion of a medical procedure. The trend lines associated with the increasing risk level 1310-2 represent trend lines of collected time series data for the given feature which indicate an increased likelihood of developing a complication following the completion of a medical procedure. The trend lines associated with the high-risk level 1310-3 represent trend lines of collected time series data for the given feature which indicate that the individual will most likely develop a complication following the completion of a medical procedure. In FIG. 13, points 1320 on tend lines within the risk levels 1310-2 and 1310-3 represent times of an onset of the complication (e.g., arrythmia) following the completion of a medical procedure (e.g., cardiac procedure).

Although illustrative embodiments of the present disclosure have been described herein with reference to the accompanying figures, it is to be understood that the disclosure is not limited to those precise embodiments, and that various other changes and modifications may be made therein by one skilled in the art without departing from the scope of the appended claims.

We claim:

1. A system, comprising:
a plurality of sensors configured to monitor physiological signals from an individual that has undergone a medical procedure on an anatomical feature, wherein the physiological signals comprise primary physiological signals which are indicative of a function of the anatomical feature, and secondary physiological signals which are monitored concurrently with the primary physiological signals;
a physiological signal processing system configured to analyze the physiological signals and extract features from the physiological signals, which are indicative of the function of the anatomical feature, following the medical procedure on the anatomical feature, the physiological signal processing system comprising:
a waveform extraction module configured to generate primary signal waveforms from the primary physiological signals, and generate secondary signal waveforms from the secondary physiological signals;
a waveform synchronization module configured to time-synchronize the primary signal waveforms with the secondary signal waveforms;
a waveform segment grouping module configured to group segments of the primary signal waveforms into self-similar groups of segments based on the time-synchronized primary and secondary signal waveforms; and
a waveform feature extraction module configured to extract features from the segments of the self-similar groups of segments of the primary signal waveforms; and
a feature analysis system configured to analyze the extracted features associated with at least one of the self-similar groups of segments to predict a risk of the individual developing a post-procedural dysfunction of the anatomical feature as a result of the medical procedure on the anatomical feature.

2. The system of claim 1, wherein the plurality of sensors comprise at least one of (i) sensor devices that are worn by the individual, and (ii) sensor patches that are coupled to the individual's skin.

3. The system of claim 1, wherein the physiological signal processing system is configured to extract features indicative of the function of the anatomical feature, from the physiological signals that are obtained over a target monitoring period following the medical procedure, wherein the target monitoring period is one of: (i) less than an hour, (ii) about an hour, (iii) multiple hours, (iv) about a day, (v) multiple days, (vi) about a week, and (viii) multiple weeks, and wherein the physiological signals are obtained and analyzed one of continuously and intermittently during the target monitoring period.

4. The system of claim 1, wherein:
the medical procedure comprises a structural heart procedure;
the primary physiological signals comprise electrocardiogram signals;
the waveform extraction module is configured to generate electrocardiogram signal waveforms from the electrocardiogram signals;
the waveform feature extraction module is configured to extract a plurality of features from segments of the self-similar groups of segments of the electrocardiogram signal waveforms, which are indicative of intra-cardiac conduction over a plurality of cardiac cycles, wherein the plurality of extracted features comprise one or more of (i) waveform features comprising one or more of P-waves, T-waves, QRS-waves, U-waves, R-R intervals, PR timing intervals, QT timing intervals, QRS timing intervals, ST segments, and PR segments, and (ii) morphological features of the waveform features; and
the morphological features of the waveform features comprise one or more of a waveform shape, a waveform contour, a waveform amplitude, a waveform width, a waveform phase, a waveform polarity, a notch, a local inversion, a ripple, an amplitude change, relative timing or polarity inversion thereof, a perturbation, a repetitive perturbation, a low amplitude, high frequency wavelet, and a wavelet that repeats along with essentially a same period as a parent waveform.

5. The system of claim 4, wherein:
the secondary physiological signals comprise one or more of an electromyogram signal, a respiratory rhythm signal, blood pressure signal, blood pressure surrogate waveform signal, a heart movement signal, a body movement signal, a phonogram, and a cardiac output signal; and
the waveform synchronization module is configured to time-synchronize the electrocardiogram signal waveforms with the secondary signal waveforms;
the waveform segment grouping module is configured to organize segments of the cardiac cycles of the electrocardiogram signal waveforms into self-similar groups of segments based on the time-synchronized electrocardiogram and secondary signal waveforms;
the waveform feature extraction module is configured to extract the plurality of features from segments of the cardiac cycles within the same self-similar groups of segments; and
the feature analysis system is configured to compare extracted features from segments of the cardiac cycles within the same self-similar groups of segments to predict a risk of the individual developing heart dysfunction.

6. The system of claim 1, wherein the feature analysis system is configured to:
compute a trend line for at least one extracted feature of the plurality of extracted features based on time series data collected for the at least one extracted feature;
compare the computed trend line with known trend lines for the at least one extracted feature as determined from a cohort patient population;
risk stratify the computed trend line based on a result of comparing of the computed trend line with the known trend lines; and render and display at least one of the time series data and the computed trend line for the at least one extracted feature on a display system.

7. The system of claim 6, wherein the feature analysis system is configured to:
risk stratify the computed trend line into one of a plurality of zones comprising a low-risk zone, an increasing risk zone, and a high-risk zone; and
generate an alert notification when an extracted feature is determined to enter into the high-risk zone.

8. The system of claim 6, wherein the feature analysis system comprises a classification module which is configured to:
utilize a neural network to process time series data of at least one extracted feature of the plurality of extracted features from the segments of self-similar groups of segments of the primary signal waveforms; and
classify a risk profile of the at least one extracted feature based on processing results of the time series data applied to the neural network.

9. A method comprising:
monitoring physiological signals from an individual that has undergone a medical procedure on an anatomical feature, wherein the physiological signals comprise primary physiological signals which are indicative of a function of the anatomical feature, and secondary physiological signals which are monitored concurrently with the primary physiological signals;
processing the physiological signals to extract features from the physiological signals which are indicative of the function of the anatomical feature, following the medical procedure on the anatomical feature, wherein processing the physiological signals comprises:
generating primary signal waveforms from the primary physiological signals;
generating secondary signal waveforms from the secondary physiological signals;
time-synchronizing the primary signal waveforms with the secondary signal waveforms;
grouping segments of the primary signal waveforms into self-similar groups of segments based on the time-synchronized primary and secondary signal waveforms; and
extracting features from the segments of the self-similar groups of segments of the primary signal waveforms; and
analyzing the extracted features associated with at least one of the self-similar groups of segments to predict a risk of the individual developing a post-procedural dysfunction of the anatomical feature as a result of the medical procedure on the anatomical feature.

10. The method of claim 9, wherein monitoring the physiological signals comprises obtaining the physiological signals from at least one of (i) sensor devices that are worn by the individual, and (ii) sensor patches that are coupled to the individual's skin.

11. The method of claim 9, wherein the physiological signals are obtained over a target monitoring period following the medical procedure, wherein the target monitoring period is one of: (i) less than an hour, (ii) about an hour, (iii) multiple hours, (iv) about a day, (v) multiple days, (vi) about a week, and (viii) multiple weeks, and wherein the physiological signals are obtained and analyzed one of continuously and intermittently during the target monitoring period.

12. The method of claim 9, further comprising:
computing a trend line for at least one extracted feature of the plurality of extracted features based on time series data collected for the at least one extracted feature;
comparing the computed trend line with known trend lines for the at least one extracted feature as determined from a cohort patient population;
risk stratifying the computed trend line based on a result of comparing of the computed trend line with the known trend lines; and
rendering and displaying at least one of the time series data and the computed trend line for the at least one extracted feature on a display system.

13. The method of claim 12, wherein risk stratifying the computed trend line comprises risk stratifying the computed trend line into one of a plurality of zones comprising a low-risk zone, an increasing risk zone, and a high-risk zone.

14. The method of claim 13, further comprising generating an alert notification when an extracted feature is determined to enter into the high-risk zone.

15. A computer program product, comprising:
one or more computer readable storage media, and program instructions collectively stored on the one or more computer readable storage media, the program instructions comprising:
program instructions to monitor physiological signals from an individual that has undergone a medical procedure on an anatomical feature, wherein the physiological signals comprise primary physiological signals which are indicative of a function of the anatomical feature, and secondary physiological signals which are monitored concurrently with the primary physiological signals;
program instructions to process the physiological signals to extract features from the physiological signals which are indicative of the function of the anatomical feature, following the medical procedure on the anatomical feature, wherein the program instructions to process the physiological signals comprise:
program instructions to generate primary signal waveforms from the primary physiological signals;
program instructions to generate secondary signal waveforms from the secondary physiological signals;
program instructions to time-synchronize the primary signal waveforms with the secondary signal waveforms;
program instructions to group segments of the primary signal waveforms into self-similar groups of segments based on the time-synchronized primary and secondary signal waveforms; and
program instructions to extract features from the segments of the self-similar groups of segments of the primary signal waveforms; and
program instructions to analyze the extracted features associated with at least one of the self-similar groups of segments to predict a risk of the individual developing a post-procedural dysfunction of the anatomical feature as a result of the medical procedure on the anatomical feature.

16. The computer program product of claim 15, wherein the program instructions to monitor the physiological signals comprise program instructions to obtain the physiological signals from at least one of (i) sensor devices that are worn by the individual, and (ii) sensor patches that are coupled to the individual's skin.

17. The computer program product of claim 15, wherein the physiological signals are obtained over a target monitoring period following the medical procedure, wherein the target monitoring period is one of: (i) less than an hour, (ii) about an hour, (iii) multiple hours, (iv) about a day, (v) multiple days, (vi) about a week, and (viii) multiple weeks, and wherein the physiological signals are obtained and analyzed one of continuously and intermittently during the target monitoring period.

18. The computer program product of claim 15, further comprising:
   program instructions to compute a trend line for at least one extracted feature of the plurality of extracted features based on time series data collected for the at least one extracted feature;
   program instructions to compare the computed trend line with known trend lines for the at least one extracted feature as determined from a cohort patient population;
   program instructions to risk stratify the computed trend line based on a result of comparing of the computed trend line with the known trend lines; and
   program instructions to render and display at least one of the time series data and the computed trend line for the at least one extracted feature on a display system.

19. The computer program product of claim 18, wherein the program instructions to risk stratify the computed trend line comprise program instructions to risk stratify the computed trend line into one of a plurality of zones comprising a low-risk zone, an increasing risk zone, and a high-risk zone.

20. The computer program product of claim 19, further comprising program instructions to generate an alert notification when an extracted feature is determined to enter into the high-risk zone.

* * * * *